(12) United States Patent
Haklai et al.

(10) Patent No.: US 6,492,128 B1
(45) Date of Patent: Dec. 10, 2002

(54) DRUG SCREEN TARGETING LIPOPROTEIN-MEMBRANE ANCHORAGE

(75) Inventors: Roni Haklai, Ramat-Gan (IL); Ariella Paz, Kefar-Saba (IL); Yoel Kloog, Herzlia (IL)

(73) Assignee: Ramot University Authority for Applied Research & Industrial Development, Ltd. (IL)

( * ) Notice: Subject to any disclaimer, the term of this patent is extended or adjusted under 35 U.S.C. 154(b) by 0 days.

(21) Appl. No.: 09/555,871
(22) PCT Filed: Feb. 26, 1998
(86) PCT No.: PCT/US98/03669
  § 371 (c)(1), (2), (4) Date: Jun. 7, 2000
(87) PCT Pub. No.: WO98/38509
  PCT Pub. Date: Sep. 3, 1998

Related U.S. Application Data

(60) Provisional application No. 60/038,518, filed on Feb. 26, 1997.

(51) Int. Cl.$^7$ ............... G01N 33/53; G01N 33/574; G01N 33/48; G01N 33/567; C12Q 1/48
(52) U.S. Cl. ............ 435/7.2; 435/7.23; 435/7.9; 435/15; 435/21; 436/63; 436/503; 436/504
(58) Field of Search ................. 435/7.2, 7.23, 435/7.9, 15, 21; 436/63, 503, 504

(56) References Cited

U.S. PATENT DOCUMENTS

| | | | |
|---|---|---|---|
| 5,185,248 A | 2/1993 | Barbacid et al. | 435/15 |
| 5,268,272 A | 12/1993 | Mullner et al. | 435/52 |
| 5,705,528 A | 1/1998 | Kloog | 514/524 |

FOREIGN PATENT DOCUMENTS

| | | |
|---|---|---|
| EP | 0 528 486 A | 2/1993 |
| WO | WO 94 13818 | 6/1994 |
| WO | WO 97 20573 | 6/1997 |
| WO | WO 97/22717 | 6/1997 |

OTHER PUBLICATIONS

Denhardt, Biochemical Journal 318(3):729–747 (1996).
Marom, et al., The Journal of Biological Chemistry 270(38):22263–22270 (1995).
Omer, et al., Molecular Microbiology 11(2):219–225 (1994).
Haklai, et al., Biochemistry 37:1306–1314 (1998).
Gibbs, Cell 65(1):1–4 (1991).

*Primary Examiner*—Hankyel T. Park
(74) *Attorney, Agent, or Firm*—Lerner, David, Littenberg, Krumholz & Mentlik, LLP

(57) ABSTRACT

A drug screening assay for identifying compounds for their potential effects on the long chain fatty acid dependant intracellular membrane anchorage sites of lipoproteins. Membranes-anchoring-target are incubated in the presence of the compound to be tested and the proportion of the target that is released by the compound is detected and quantitated. The benchmark for this assay are the prenylated proteins such as the farnesylated and palmitoylated oncogenic ras trigger proteins which are displaced from their anchorage at the intracellular plasma membrane by derivatives of Farnesyl Thiosalicylic Acid (FTS). The assay is adaptable to flexibly assay a large variety of anchored targets using a wide range of labeling and detection techniques in test wells, tissue culture, and in animals as injected cells or transgenic, thereby directly addressing a wide range of pharmacologically relevant needs.

33 Claims, 15 Drawing Sheets

PARTICULATE

CYTOSOL

RAS ⇒
FTS (μM)  0  50  25  10  5  ·
AFC (μM)  ·   ·   ·   ·   ·  50

Gβ₃₇ ⇒
　　　　C　RAS

RAS ⇒
　　　　C　RAS

EJ CELLS

RAS ⇒
FTS (μM)  0   5   10   25   50

RAT1 CELLS

RAS ⇒
FTS (μM)  0   5   10   25   50

DRUG SCREEN TARGETING LIPOPROTEIN-MEMBRANE ANCHORAGE

This application is a §371 application of PCT/US98/03669, filed Feb. 26, 1998, which claims the benefit of U. S. Provisional Application No. 60/038,518, filed Feb. 26, 1997 pursuant to §119(e).

This invention relates to screening assays. Specifically, this invention relates to screening assays to identify compounds that effect signal transducing protein phosphorylation cascades by targeting the membrane anchor of long chain fatty acid modified trigger proteins. More specifically, this invention relates to drug screens to identify drugs that effect ligand mediated signal transducing protein phosphorylation cascades (for example; Ras/Rho mediated signal transducing protein phosphorylation cascades) by effecting the long chain fatty acid dependent membrane anchorage of long chain fatty acid modified trigger proteins (for example; prenylated or palmitoylated trigger proteins).

BACKGROUND OF THE INVENTION

Multicellular organisms have a multiplicity of specialized cells functioning in cooperation. Communication in the organism to coordinate cooperative functions is mediated by a number of well known messengers, for example: hormones, neurotransmitters, cytokines, etc. The messengers communicate by binding a receptor at the cell membrane. The receptor binding activates a desired cell function. Alternatively, and/or additionally, cell functions are activated in response to signals generated and received intracellularly. The identification and characterization of the molecules involved, and the elucidation of mechanisms whereby such molecules cooperatively regulate the functions and link the signals to those functions, is one of the great scientific advances of the past few decades.

Membrane associated receptors are exquisitely specific for ligands (signal molecule) such as hormones. Any one cell exhibits a multiplicity of these receptors, the composition of which defines the types of signals to which that cell responds functionally. The receptors are often associated within the membrane superstructure with trigger proteins. When such a receptor binds the signal molecule it activates the trigger protein. These trigger proteins are in turn linked to initiate a cascade of regulatory molecules leading to the appropriate function of the cell that is activated by the hormone. A review of such a receptor→trigger→cascade→function phenomenon is provided in Denhardt, D. T., *Signal-transducing Protein Phosphorylation Cascades Mediated by Ras/Rho Proteins in the Mammalian Cell: The Potential for Multiplex Signaling,* 318 Biochem. J. 729–747 (1996) ("Denhardt"), the entirety of which is incorporated herein by reference.

Each trigger protein associates with specific membranes in the cell and the activity, and also often the specificity, of the protein is dependent on the trigger protein being associated with the correct membrane. To accomplish this the protein is often modified by one or more long chain fatty acids. Sometimes the protein is also carboxymethylated, glycosylated, cleaved, etc. but it appears that the most essential modification for directing many proteins to insert into the proper membrane is the long chain fatty acid modification(s).

One significant example set are cellular Ras proteins, extensively studied because mutated forms, oncogenic Ras proteins, are involved in the generation of many types of cancer. Ras is modified at its carboxy-terminus with a prenyl group and at a mid-chain Cys with a palmitoyl group. Conceptually, for Ras to be active it must be prenylated and anchored in the membrane. The prenylation of such trigger proteins as Ras, and many other related proteins, is reviewed in Omer, C A, and J. B. Gibbs, *Protein Prenylation in Eukaryotic Microorganisms: Genetics, Biology, and Biochemistry,* 11 Molecular Microbiology 219–225 (1994) ("Omer & Gibbs"), the entirety of which is incorporated herein by reference.

In brief, referring to FIG. 1, an immature trigger protein 1 is processed in the cell by the addition of a prenyl group 2 to a C-terminal cysteine. This prenylation reaction, catalyzed by a prenylprotein-transferase 3, is one of the processing reactions that results in the production of a mature prenylated trigger protein 4. Prenylated trigger protein 4 attaches to a trigger protein anchorage site 6 in a cellular membrane 5 resulting in a membrane anchored prenylated trigger protein 4'.

Membrane anchored prenylated trigger protein 4' is stable and fully mature, yet remains inactive until an effector 7 activates it via a signal 8 acting on membrane receptor 6. Signal 8 can arise on either face of the membrane or can be both intracellular and extracellular. Such a signal can be activating or inactivating. If activating, as illustrated in this figure, membrane anchored prenylated trigger protein 4' becomes an activated prenylated trigger protein 9. Activated prenylated trigger protein 9 has an enzymatic or binding activity that launches a regulatory cascade 10 of reactions. The reactions of regulatory cascade 10 link activated prenylated trigger protein 9 to a cellular function 11. Cellular function 11 consists of one or a set of cellular actions that define the specialized function of the activated cell. This cascade activation system allows a single trigger event to regulate multiple cell actions that must work in concert to accomplish a particular cell function, such as cellular growth or division.

There are numerous examples of signal transducing regulatory trigger pathways of the type generalized in FIG. 1. Denhardt defines various mammalian trigger proteins (including the gene products of Ras superfamily, and other G-proteins or GTP-binding proteins) and associated function cascades.

Briefly:
the Ras family, including H-ras, N-ras, Ka-ras, and Kb-ras, partition to specific membranes depending on the type of prenylation and, among other functions, regulate cell cycling and adhesion (mutations of ras, known as oncogenic ras, are involved in the formation of some types of tumors);
the Rap family, found in granules of Golgi and ER antagonize ras function (Rap 1A, also known as Krev-1, antagonizes the Kras oncogene);
the Ra1 family, including Ra1-a and Ra1-B appear to regulate the activity of exocytic and endocytic vesicles;
the Rho family, which includes Rho-A, Rho-B, Rho-C, Rac-1, Rac-2, CDC42, Rho-G, and TC10, play dynamic roles in the regulation of the actin cytoskeleton and focal contacts mediating formation of filopodia and lamellipodia (Rac also controls NADPH oxidase activity in phagocytes);
the Ran proteins are involved in the transport of RNA and protein across the nuclear membrane;
the ARF/SAR proteins are important for vesicle formation and budding;
and the large and extensively studied
Rab/Ypt family are involved both in regulating intracellular vesicle trafficking between donor and acceptor membrane-enclosed compartments and in controlling the exocytosis and endocytosis of different types of vesicles.

In addition to the trigger protein—cascade systems reviewed in Denhardt, other systems have also been described and extensively studied. For example, a family of myristoylated proteins are described that have a myristoyl group (C14:0) covalently attached, via amide linkage, to the NH$_2$-terminal glycine residue of certain cellular and viral proteins. The attachment is catalyzed by myristoyl-CoA:protein N-myristoyltransferase (NMT) as a cotranslational modification. Compounds that block NMT activity have been shown to be potentially useful as anti-fungal, anti-viral, and anti-parasitic agents, and are therefore postulated to be useful for treating intracellular pathogens. A list of references and U.S. Patents detailing the myristoylation trigger protein system are found in table 1 each the entirety of which is incorporated herein by reference.

It appears that in order for most trigger proteins to become mature and capable of regulating a function cascade they must be long chain fatty acid modified and associated with the appropriate cell membrane anchor. Omer & Gibbs describe modification by prenylation of Ras superfamily encoded proteins, wherein, three enzymes are identified that mediate prenylation; farnesyl protein transferase, geranylgeranyl protein transferase type I, and geranylgeranyl protein transferase type II. These three enzymes, depicted generally in FIG. 1 as prenyl protein transferase 3, have become the target for the development of a number of drugs. Farnesyl protein transferase is the subject of at least 46 U.S. patents since 1992, listed herewith in appended Table 2, each the entirety of which is incorporated herein by reference.

In addition to prenylation, palmitoylation is essential to membrane anchorage of some of the RAS superfamily members listed in table 2, as well as many other membrane associated trigger proteins. Articles describing the palmitoylation of various other membrane associated cellular proteins and the relevance of palmitoylation to their cellular function, are listed in appended Table 3, each the entirety of which is incorporated herein by reference.

Inhibitors of farnesyl protein transferase block the maturation of farnesylated trigger proteins and prevent them from associating with the appropriate membrane. For example, drug developers look for compounds that block the activity of Oncogenic Ras ("OncRas") activity without effecting normal Ras. To accomplish this they screen for compounds that preferentially block the farnesylation of OncRas and not normal Ras by farnesyl protein transferase. Since farnesylation is necessary for maturation and association of Ras or OncRas with the plasma membrane, a drug that blocks the farnesylation of OncRas necessarily blocks its activity.

Farnesyl protein transferase inhibitors are attractive to drug developers because of their potential for treatment on many types of cancer. OncRas, a mutated form of Ras, is directly implicated as the cause of most pancreatic tumors and more than 50% of colon cancer cases. Additionally, permanent activation of Ras by over-production of hormones and growth factors is implicated as the causative agent in tissue specific growth factor induced tumors. Besides tumor treatment, farnesyl protein transferase inhibitors as well as geranyl derivatized inhibitors are being developed for cholesterol reduction and treatment of atheroscleroses.

The main conceptual drawback of developing inhibitors of specific prenyl protein transferases is that these enzymes play significant critical roles in a multiplicity of normal cellular processes. Such a drawback may explain the difficulties encountered by drug developers who have developed inhibitors of these enzymes. Such difficulties include incomplete enzyme inhibition, toxicity, and non-specificity. In this regard, this application describes a method of identifying drugs that displace mature prenylated trigger protein from their membrane anchor site rather than inhibiting their prenylation by protein prenyl transferases.

OBJECTS AND SUMMARY OF THE INVENTION

It is first object of this invention to overcome the drawbacks and inconveniences of the prior art. In that regard, it is an object of the present invention to provide a drug screen, including the steps of: providing an assay material, the assay material including a specific membrane and a specific membrane anchored target protein, and the assay material having a known quantity of the specific membrane anchored target protein associated with the specific membrane.

Exposing the assay material to a compound that is being tested for the compound's ability to disrupt membrane association of the specific membrane anchored target protein. Separating the assay material into a membrane fraction of the specific membrane and a cytosolic fraction of a balance of the assay material remaining after the specific membrane is removed. And, at least one of determining a fraction of the known quantity that is a released quantity of target protein in the cytosolic fraction and determining a fraction of the known quantity that is a non-released quantity of target protein in the membrane fraction.

It is another object of the present invention to provide a method of testing a compound for its effect on specific lipoprotein membrane anchorage, including the steps of: labeling the lipoprotein with a tag, exposing the membrane anchorage to the compound, and at least one of detecting a membrane-disassociated tag concentration and detecting a membrane associated tag concentration.

It is another object of the present invention to provide a drug screen, including the steps of: providing an assay material, the assay material including a specific membrane and at least one target anchored in the specific membrane, and the assay material having a determinable quantity of the target, exposing the assay material to a compound that is being tested for the compound's ability to release membrane association of the target from the specific membrane, and at least one of determining a fraction of the determinable quantity that is a released quantity of the target and determining a fraction of the determinable quantity that is a non-released quantity of the target.

It is a feature that the drug screen further includes the step of labeling the specific membrane anchored protein with a detectable tag whereby the known quantity is trackable following fractionation by detecting the tag. Also, the step of determining a fraction of the known quantity that is a released quantity of target protein in the cytosolic fraction is accomplished by determining a quantity of the tag in the cytosolic fraction, and the step of determining a fraction of the known quantity that is a non-released quantity of target protein in the membrane fraction is accomplished by determining a quantity of the tag in the membrane fraction.

It is a further feature of the drug screen that the step of labeling is one selected from the group consisting of genetic labeling, metabolic labeling, chemical labeling, immunologic labeling, and labeling by identification of an intrinsic characteristic of the specific membrane anchored target protein, and the tag is at least one selected from the group consisting of green fluorescent protein, Alkaline Phosphatase, Horseradish Peroxidase, Urease, β-galactosidase, CAT, Luciferase, an immunogenic tag peptide sequence, an extrinsically activatable enzyme, an extrinsically activatable toxin, an extrinsically activatable fluor, an extrinnsicly activatable quenching agent, a radioactive element, and an antibody.

It is a further feature of the drug screen that the specific membrane is at least one of a plasma membrane, a nuclear membrane, a endoplasmic reticulum, a golgi, and a vesicle.

It is a further feature of the drug screen that the target protein has at least one long chain fatty acid group.

It is a further feature of the drug screen that the long chain fatty acid group is at least one of a prenyl, a myristoyl, and a palmitoyl.

It is a further feature of the drug screen that the prenyl is selected from the group consisting of a farnesyl, a geranyl, and a geranylgeranyl.

It is a further feature of the drug screen that the target protein is at least one selected from the group consisting of; the Ras family proteins, including H-ras, N-ras, Ka-ras, and Kb-ras, the Rap family proteins, the Ral family proteins, including Ra1-a and Ra1-B, the Rho family proteins, which includes Rho-A, Rho-B, Rho-C, Rac-1, Rac-2, CDC42, Rho-G, and TCIO, the Ran proteins, the ARF/SAR proteins, the Rab/Ypt family proteins, the family of myristoylated proteins; and the family of trimeric G-proteins.

It is another feature that the drug screen further includes the step of labeling the target with a detectable tag whereby the known quantity of target protein is trackable following fractionation by detecting the tag.

It is another feature that the drug screen further includes the step of providing a label gene in a cell whereby a release of the at least one target from the specific membrane causes the label gene to one of ceasing expression and commencing expression.

In summary, the present invention is a drug screening assay for identifying compounds for their potential effects on the long chain fatty acid dependent intracellular membrane anchorage sites of lipoproteins. Membranes-anchoring target are incubated in the presence of the compound to be tested and the proportion of the target that is released by the compound is detected and quantitated.

The benchmark for this assay are the prenylated proteins such as the farnesylated oncogenic ras trigger proteins which are displaced from their anchorage at the intracellular plasma membrane by Farnesyl Thiosalicylic Acid (FTS) and derivatives of FTS. The assay is adaptable to flexibly assay a large variety of anchored targets using a wide range of labeling and detection techniques in test wells, tissue culture, and in animals, as injected cells or transgenics, thereby directly addressing a wide range of pharmacologically relevant questions.

The above, and other objects, features and advantages of the present invention will become apparent from the following description read in conjunction with the accompanying drawings, in which like reference numerals designate the same elements.

SUMMARY OF THE DRAWINGS

FIGS. 3a–c examples the results of experiments directed to the kinetics of FTS dislodging of oncogenic Ras from the membranes of EJ cells, wherein:

FIG. 3a demonstrates the amount of Ras remaining associated with the membrane after various time intervals in presence of FTS;

FIG. 3b demonstrates the amount of Ras that has moved into the cytosol after various time intervals in presence of FTS; and FIG. 3c is a graphical representation of the data derived from a densitometric scanning of bands such as those exampled in FIGS. 3a and 3b;

FIGS. 4a–d illustrate the results of experiments directed to the specificity of FTS dislodging Ras, wherein:

FIG. 4a demonstrates the dose response of FTS to dislodge oncogenic Ras in EJ cells in comparison with the lack of effect of Ras anchorage by AFC;

FIG. 4b is a graphical representation, of the dose response of FTS effect on oncogenic Ras in EJ cells, derived from a densitometric scanning of immunoblots such as is exampled in FIG. 4a.

FIG. 4c demonstrates the lack of FTS effect on $G\beta_{37}$ anchorage in EJ cells; and FIG. 4d demonstrates the effect FTS on normal Ras anchorage in Rat1 cells.

FIGS. 5a–d illustrate the results of experiments directed to the effect of FTS on total Ras, wherein:

FIG. 3a demonstrates the dose response effect of FTS on total oncogenic Ras in EJ cells;

FIG. 5b is a graphical representation of the dose response of FTS effect on oncogenic Ras in EJ cells, derived from a densitometric scanning of immunoblots such as is illustrated in FIG. 5a;

FIG. 3c demonstrates the dose response effect of FTS on total Ras in Rat1 cells; and FIG. 5d is a graphical representation of the dose response of FTS effect on Ras in Rat1 cells, derived from a densitometric scanning of immunoblots such as is illustrated in FIG. 5c.

FIG. 6b is a graphical representation, of the time kinetics of FTS effect on Ras in EJ cells, derived from a densitometric scanning of immunoblots such as is illustrated in FIG. 6a.

FIGS. 7a–b illustrate the results of experiments directed to the effect of FTS on oncogenic Ras anchorage in isolated EJ cell membranes, wherein:

FIG. 7a demonstrates the dose response effect of FTS on total oncogenic Ras in EJ cell membranes; and FIG. 7b is a graphical representation of the dose response of FTS effect on oncogenic Ras in EJ cell membranes, derived from a densitometric scanning of immunoblots such as is illustrated in FIG. 7a.

DETAILED DESCRIPTION OF THE PREFERRED EMBODIMENTS

The Drug Screening Assay

Figure 1:
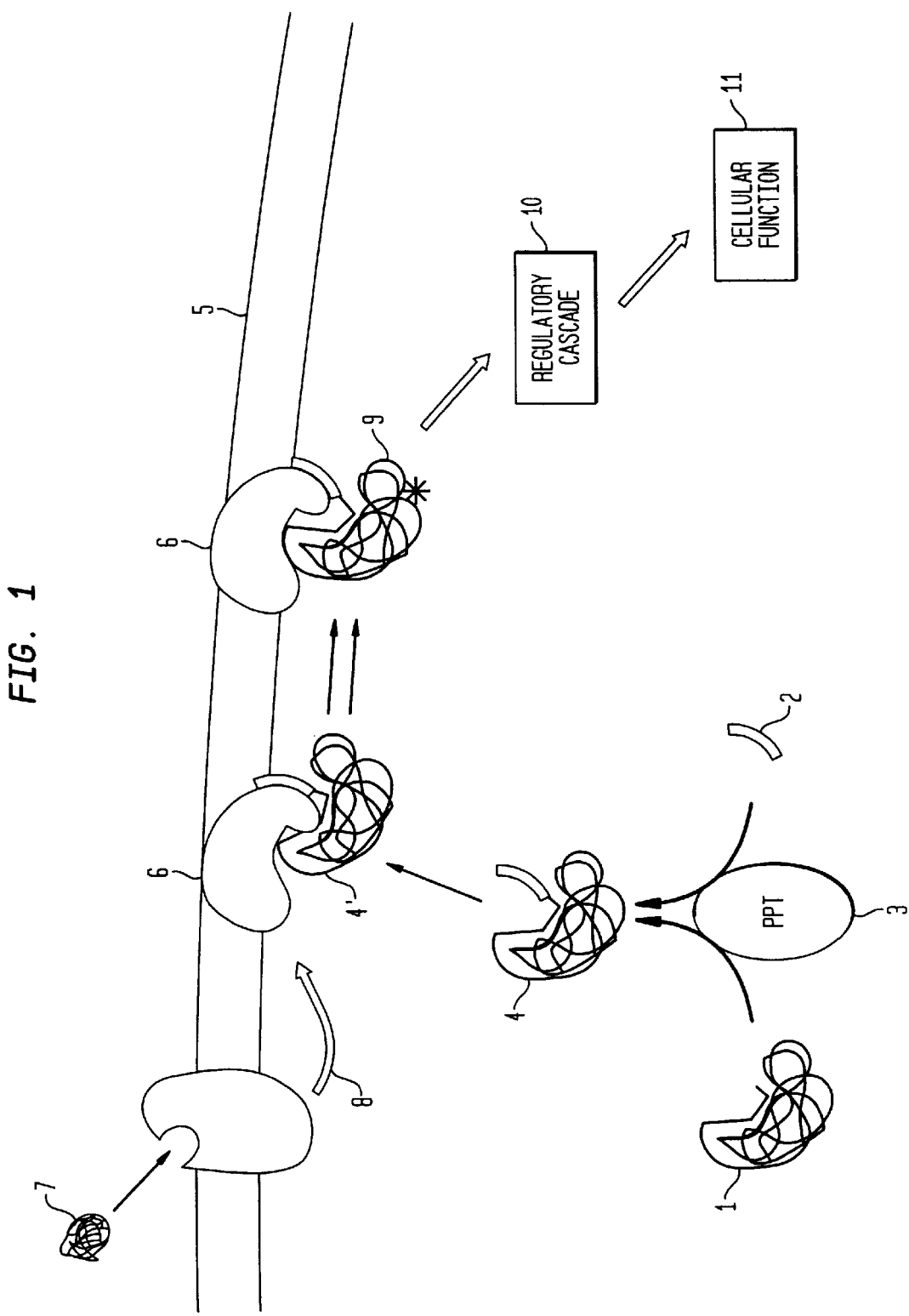
FIG. 1 is a cartoon illustrating the generation and function of a hypothetical generic target protein that is anchored to the membrane by way of a lipoprotein anchor associated receptor.

Referring to FIG. 1, the anchorage of membrane anchored prenylated trigger protein 4' to trigger protein anchorage site 6 in cellular membrane 5 is the target for the present invention. Compounds are screened for their potential to attack this anchorage site and release membrane anchored prenylated trigger protein 4' from cellular membrane 5 allowing its degradation. Three levels of screening, utilizing the present invention, are outlined here as examples: a cell free initial screening, an in vitro screen utilizing a cell culture, and an in vivo screen utilizing injected cells or transgenic animals.

General Assay Principle

Figure 2:
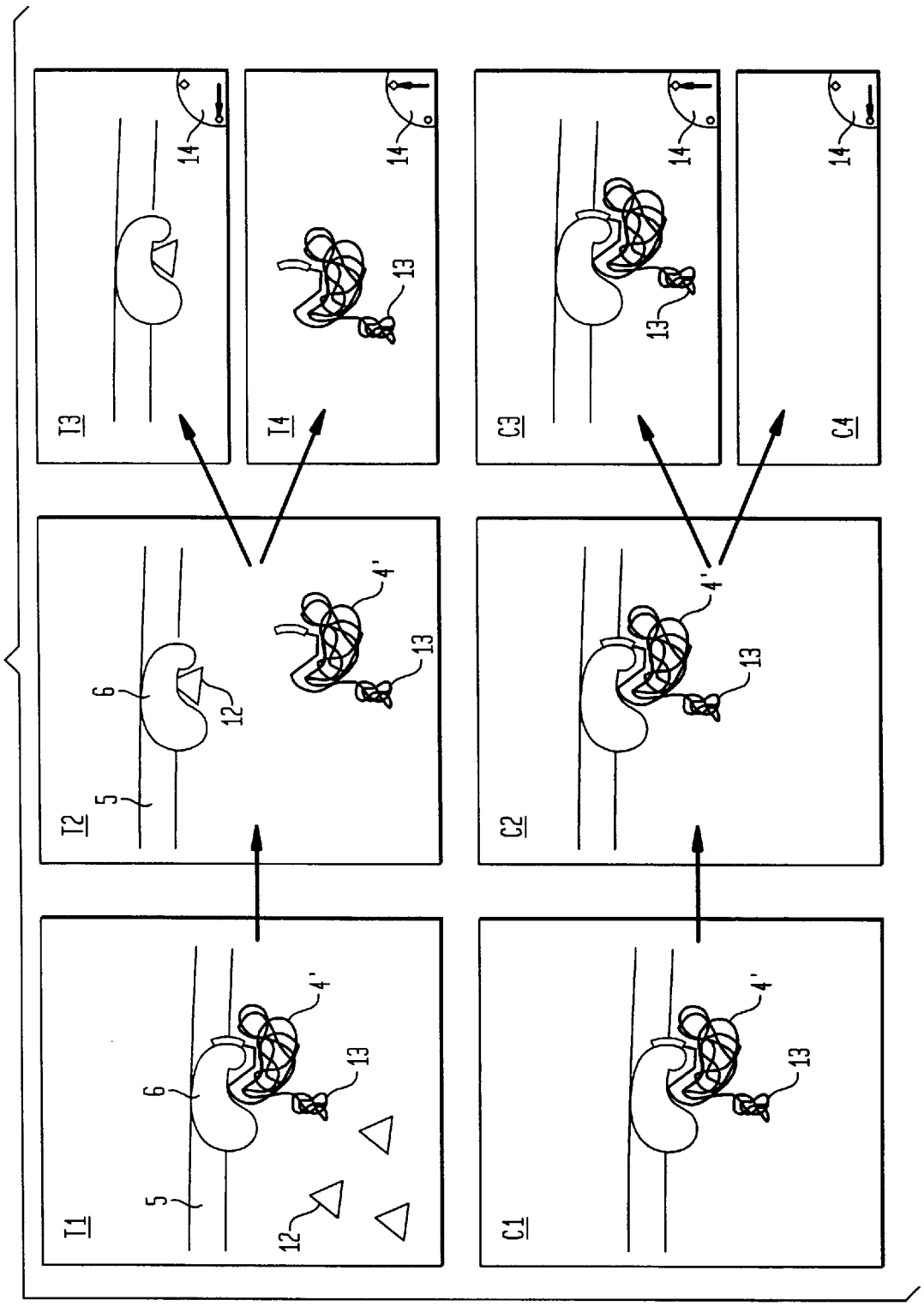
FIG. 2 is a paneled cartoon illustration of the drug screen of the present invention being applied to the hypothetical of FIG. 1.

Referring to FIG. 2, a test series beginning at panel T1 depicts the assay of the present invention as performed in the presence of a drug 12 to be tested. Membrane anchored prenylated trigger protein 4' is generated with a standard molecular tag 13 that can be detected and quantitated by a detector 14. In the presence of drug 12, membrane anchored prenylated trigger protein 4' dissociates along with molecular tag 13 from trigger protein anchorage site 6, as illustrated in panel T2, and becomes part of the soluble phase. Once the dissociation occurs, separation of cellular membrane 5 from the soluble phase is performed thereby separating any remaining membrane anchored prenylated trigger protein 4' from that which has become disassociated.

Illustrated here, drug 12 effectively removed the target trigger protein from its membrane receptor; shown in panel T3, the membrane fraction, detector 14 indicates low concentration of molecular tag 13, as compared to panel T4, the soluble fraction, where detector 14 indicates high concentration of molecular tag 13. In a control series, panels C1–C4, or a test series (T1'–T4' not shown) where the drug is ineffective, the membrane fraction, panel C3 or T3', would show detector 14 indicating high concentration of molecular tag 13, while the soluble fraction, panel C4 or T4', would show detector 14 indicating low concentration of molecular tag 13. In reality the effect of dislodging the target protein from its membrane may only be a transient increase of cytosolic target and molecular tag 13 because the target may be degraded over time by cytoplasmic proteases. This would result in a decreased total cell target and molecular tag 13 concentration (membrane fraction concentration plus soluble fraction concentration). The ability to detect a decrease or increase of total cell target protein concentration as a result of a test compound is contemplated as a feature of the assay of the present invention.

Assays

The general assay principle illustrated in FIG. 2 is adaptable for use in cell free systems, in vitro, and in vivo.

Cell Free Assay

For the cell free assay the tagged target protein is generated in an appropriate cell line. Membranes with the tagged target protein are separated, purified, and stored as a reagent for use in the assay. Large batches of membranes can be generated and pooled to allow standardization. To run the assay a standard aliquot of membrane is incubated with a known concentration of drug under standardized conditions. The membrane and soluble fractions are separated and either the soluble fraction alone or both the soluble and membrane fractions are assayed for the presence of the tagged target protein. An increase redistribution of the molecular tag to the soluble fraction indicates the effectiveness of the drug at dislodging the target protein from its membrane anchor.

In Vitro Assay

The intact cells that are appropriate for generating membranes for the cell free assay, supra, can be used directly in assays to screen the in vitro effect of a drug on membrane anchoring of the tagged target protein. Here a standardized number of cells (determined by cell enumeration or total protein determination) are incubated with a known concentration of the compound to be tested under standardized conditions. The cells are then subjected to fractionation to separate the membranes from the cytosol. Then cytosolic and membrane fractions are assayed for the presence of the tagged target protein. Alternatively the cells may be assayed directly, without fractionation, by the presence of a reporter that is expressed only when the target is released from the membrane. A redistribution of the molecular tag to the cytosolic fraction indicates the effectiveness of the compound at dislodging the target protein from its membrane anchor.

In Vivo Assay

Cells that have been generated for use in the in vitro assay can be adapted for in vivo use by either injecting the cells into immunologically tolerant animals or by generating transgenic animals that express the target in detectable form. In this manner, the target protein is tagged in the animal and the animal is dosed with the drug to be tested under standardized conditions. An appropriate tissue is collected and subjected to fractionation to separate the membranes from the cytosol or assayed directly by the presence of a reporter. Then cytosolic and membrane fractions are assayed for the presence of the tagged target protein. An increase redistribution of the molecular tag to the cytosolic fraction indicates the effectiveness of the drug at dislodging the target protein from its membrane anchor.

Prenylated Trigger Protein Targets

As discussed in the background section, supra, many prenylated trigger proteins are described and are within the scope of this assay method. These include but are not limited to: the Ras proteins, including H-ras, N-ras, Ka-ras, and Kb-ras; the Rap proteins (Rap 1A, also known as Krev-1, antagonizes the K-ras oncogene); the Ra1 proteins, including Ra1-a and Ra1-B; the Rho proteins, which includes Rho-A, Rho-B, Rho-C, Rac-1, Rac-2, CDC42, Rho-G, and TC10; the Ran proteins; the ARF/SAR proteins; and the Rab/Ypt proteins. The particular identities of these proteins are found in: Wagner and Williams, 266 Am. J. Physiol GI–G14 (1994); Nuofler and Balch, 83 Annu. Rev. Biochem 949–990 (1995); Rothman, 372 Nature 55–63 (London 1994); Vojtek and Cooper, 82 Cell 527–529 (1995); Chant and Stowers 81 Cell 1–4 (1995); and Ridley, 5 Curr. Opin. Genet. Dev. 24–30 (1995) each the entirety of which is incorporated herein by reference. The screening assay is also contemplated for use on heretofore undescribed trigger proteins whose activity depends on specific membrane anchoring.

In addition to prenylation. many membrane anchored proteins are dependent on Palmitoylation for membrane anchorage. Examples of such proteins are detailed in the incorporated references of the background section, supra. Some proteins such as Ras are both prenylated and palmitoylated and its anchorage in plasma membrane appears to require both modifications.

Other Long Chain Fatty Acid Modified Protein Targets

It is currently thought that trafficking of proteins to their specific membrane anchorage site is regulated by the constituency of long chain fatty acids that are used to modify the target protein. In this regard two other categories of target proteins for the assay of the present invention are contemplated. They are synthetic modified target proteins and non-prenyl/non-palmitoyl long chain fatty acid modified proteins. In the first category, genes that encode proteins that are not normally modified, are mutated to add specific fatty acid modification sites, such as C-terminal CAAX sequences. Once the mutated genes are generated they are used to generate isolated membranes, cells, or transgenic animals with the protein anchored in the membrane directed by the modification. In the second category, many long chain fatty acid modified proteins are found exclusively in specific membranes whose lipid constituencies are much less characterized than those specified above. Once these proteins are characterized it is contemplated that this assay can be utilized to assay compounds for their specific effect on the membrane anchorage of that protein.

Species and Cells (Source of Membranes)

It is contemplated that any eukaryotic species can be utilized as the source of cellular membranes and target protein. Such sources includes fresh tissue, primary tissue cultures, and transformed cell lines. The variables for determining the species/tissue/cell source include: the purpose of the screen, for example, the substance's ultimate use is as a human pharmaceutical, a veterinary pharmaceutical, an insecticide, a disinfectant, etc.; the compatibility of the target protein with the host cell; the amount known about the target protein, its genetics and its expression; etc. For example, the desire to develop a human pharmaceutical would likely dictate the use of a human cell line that normally expresses the prenylated target protein. However, if it were found that the human target protein could be expressed in mouse and behaves the same in the mouse cell that it does in the human cell, then the screening assay may be advantaged by using a mouse system. In this regard, the mouse could be host at all levels of the screen; cell free screening, in vitro screening, and in vivo screening in a transgenic.

Tagging the Prenylated Protein Target

Many labels are available for tagging the prenylated trigger protein and a variety of standard labeling methodologies are useful. Exemplified here are genetic labeling (i.e. genetically encoding the label as part of the trigger protein's gene sequence), metabolic labeling, chemical labeling, immunologic labelling, and intrinsic activity detection.

Genetic Labeling

Enzymes, fluorescent proteins, and specific binding proteins are encoded in tandem with the gene sequence for the prenylated trigger protein and transfected by means of a strongly promoted commercial expression vector into the appropriate cell. The expression of the randomly encoded sequence results in the production of a fatty acid derivatized fusion protein having the characteristics of both the target protein and the label protein. Examples of encodable label proteins that are useful in this procedure include: green fluorescent protein (GFP), Alkaline Phosphatase, Horseradish Peroxidase (HRP), Urease, β-galactosidase, CAT, and Luciferase. Encodable label proteins may also include immunogenic tag peptide sequences, or extrinsically activatable enzymes, toxins, fluores or quenching agents.

A variation on this theme, utilizing prenyl modification as an example, would include modifying a normally non-prenylated protein that has a genetic reporter activity to mimic the anchorage of the prenylated target protein. This is done by adding the prenylation site motif CAAX to the non-prenylated protein. The non-prenylated protein then becomes prenylated and anchors in the membrane. Since the modified protein is anchored in the membrane it cannot effect its normal genetic activation that causes the reporter gene expression. If a drug being screened releases the modified protein from its membrane anchor then it becomes active and causes the expression of the reporter gene. Such an example of this variation is detailed in the disclosure of embodiment VI, infra.

The methodologies for gene cloning, preparation of genetic constructs, transfection, and generation of transgenic animals and other standard techniques commonly used in molecular biology laboratories used to generate these fusion protein labels are found in standard manuals such as *Current Protocols of Molecular Biology*, John Wiley & Sons (January 1997) ("Current Protocols"), the entirety of which is herein incorporated by reference. The gene and amino acid sequences for many label proteins, as well as the gene and amino acid sequences for the trigger proteins, are readily accessible in the public databases. Commercial expression vectors and complete documentation for their use are readily available from Stratagene, Invitrogen, and others.

Metabolic Labeling

All cellular proteins of tissue culture cells are labeled by metabolic incorporation of radiolabeled agent such as $^{35}S$ Methionine (Met) or Cysteine (Cys). The radiolabeled Met or Cys are simply substituted, partially or completely, for the non-radioactive Met or Cys normally found in the tissue culture medium. The methodology is described in current protocols. Cultures grown in this way produce cells wherein all the proteins whose compositions include Met or Cys are radiolabeled and can be detected by all the normal means for detecting radioactive emissions. Since this is a general labeling, rather than a specific labeling of the target protein, the detection of the prenylated trigger protein, in the present assay, must include a purification or separation process. For example, immunoprecipitation, affinity chromatography, gel filtration, rocket immunoelectrophoresis, PAGE, etc. The methodology for these standard separation and purification procedures are also found in Current Protocols.

Chemical Labeling

Like metabolic labeling, supra, chemical labeling is also a generalized labeling and requires a separation or purification step in the detection phase. Chemical labeling attaches a tag by chemically reacting the tag to the proteins of the cell and is accomplished regardless of cell viability. $^{125}$I is generally used in this manner as is labeling with fluores, biotin, metals etc. The methodology is described in Current Protocols.

Immunologic Labelling

Immunologic labeling, unlike chemical and metabolic labeling supra,is a specific labeling and can eliminate the need for purification or separation prior to detection. With this method an antibody is developed that specifically binds the target protein. The labeling can take place prior to, simultaneous with, or after the incubation of the drugs with the membranes. If for example labeling is prior to drug exposure, the antibody is incubated with the reaction mixture and binds appropriately to the trigger protein. Unbound antibody is then washed away. Once the drug has been incubated with the membranes the fractions are separated and the antibody is detected. In systems where concentrations of target are low the antibody may be amplified by addition of a secondary antibody. Methodologies for immunologic labeling are detailed in Current Protocols.

Intrinsic Activity Detection

Some trigger proteins have intrinsic enzymatic or binding activity or unique biochemical or biophysical features that are intrinsically detectable. These features can be utilized to detect the trigger protein concentration in the separated membrane and soluble fractions after treatment with the drug. in this case no extrinsic label is needed. Examples of this type of tag includes, GTP binding capacity specific kinase activity, molecular weight, molecular size, subunit composition, species specificity Additionally, as described supra, a reporter gene may be tied to the downstream activity of the trigger protein such that the expression of the reporter gene is ongoing as long as the target trigger protein is associated with the membrane.

Separation of Membrane and Soluble Fractions

In those embodiments of the assay of the present invention that do not utilize a reporter that is detectable in intact cells responsively to the disruption of the anchorage, the detection of the tag requires the physical separation of membrane and soluble fractions. Also in the cell free assay, the membranes are separated prior to the assay of drug, standardized, aliquoted, and stored until needed. Then after the assay of drug the membranes are separated from the soluble fraction to ascertain the amount of target protein that has been dislodged from the membrane anchor. These separations are usually accomplished by centrifugation although other methods are known and are acceptable.

Prior to separation of membranes from intact cells, the cells must be disrupted. Disruption must be accomplished without solubilization of the membranes or denaturation of the proteins, therefore a mechanical disruption is preferred. Examples of mechanical disruption include ultrasonic vibration, freeze/thaw, french press, sucrose swelling, etc. (See: *Guide to Protein Purification,* 182 Methods in Enzymology (1990) the entirety of which is incorporated herein by reference). Once the cells are disrupted they are centrifuged to pellet the membranes and the aqueous (cytosolic) phase is removed and discarded if the membranes are being prepared for use in the cell free assay, or transferred to another tube if the cytosolic fraction is to be assayed for released target. The membranes are then washed with assay buffer and repelleted.

As mentioned supra, the type of long chain fatty acid modification that a particular trigger protein receives appears to be involved in the localization of some types of trigger proteins to specific membranes. For example, Ras and Ste 18 are associated with plasma membrane, Ydj1 is associated with the cytoplasmic side of nuclear membrane and endoplasmic reticulum, and Ypt1 and Sec4 are associated with the ER-Golgi-plasma membrane secretion pathway. Consequently, it is advantageous when screening some types of targets to use specialized separation techniques to isolate only those membranes where the target protein is localized. Some acceptable general and specific membrane fraction preparation methods are reported in: Fayle et al., *Isolation of plasma membrane from human blood,* 147 Europ J Biochem 409–419 (1985); Nickel et al, *ADP Ribosylation Factor and 14 kD Polypeptide are Associated with Heparan Sulfate-Carrying Post-Trans-Golgi Network Secretory Vesicles in Rat Hepatocytes,* 125 J Biol Chem 721–732 (1994); Fujiki et al., *Isolation of Intracellular Membranes by Means of Sodium Carbonate Treatment: Application to Endoplasmic Reticulum,* 93 J Biol Chem 97–101 (1982); and Bergeron et al., *Differential and Analytical Subfractionation of Rat Liver Components, Internalized Insulin, and Prolactin,* 25 Biochem 1756–1764 (1986), each the entirety of which is incorporated herein by reference.

Detection of the Tag

Once separated the membrane and aqueous fractions are tested for the presence and quantity of tagged target. The methodology for detection of the target is highly dependent on the type of tag, the methodology used in labeling, and the type of assay being performed. The various tags and their advantages and drawbacks are averred to generally in the discussion on labeling, supra.

If labelled generally (i.e. all cellular proteins become labeled), such as with metabolic and chemical labelling the target is first purified by an intermediate procedure prior to detection. For example, if the target is labelled by growing the cell line in the presence of $^{35}$S Met and Cys, all of the proteins in the cell are radiolabeled according to their Met and Cys content. Once the drug exposure portion of the assay is concluded, the cytosol and membrane fractions are subjected to affinity purification using a target specific antibody isolatable on a solid matrix, such as agarose, either by direct conjugation or by agarose conjugated secondary antibody binding. Subsequently, the affinity purified radiolabeled target is eluted from the matrix, separated by SDS-PAGE, transferred onto blotting paper or dried in the gel, and exposed to a radiosensitive film, such as X-ray film, to detect the presence of the radiolabel.

If the labelling method used is a specific labelling such as genetic labelling or immunologic labelling then the detection is much simpler. Here the fractions are measured for the presence of the tagged target by simply quantitating the tag concentration directly. For example, this can be accomplished by measuring fluorescence intensity, enzyme activity, or chemiluminescence.

Reduction-to-Practice/Proof-of-Principal Experiments

The benchmark for the screening method described in this disclosure is Farnesylthiosalicylic acid (FTS) and FTS derivatives which act on those Ras proteins that are prenylated with farnesyl, and partition to the plasma membrane. FTS inhibits the growth of Erb B2 and Ha-Ras-transformed cells in a dose-dependent manner (1–25 $\mu$m). Conversely, it does not affect the growth to v-raf or T-antigen transformed cells. (See: Marom, M., Haklai, R., Ben-Baruch, G., Marciano, D., Egozi, Y., and Y. Kloog, *Selective Inhibition of Ras-dependent Cell Growth by Farnesyl-thio-salisylic acid,* 270 J. Biol. Chem. 22263–22270 (1993)("Marom et al."); and Marciano, D., Ben-Baruch, G., Marom M., Egozi, Y., Haklai, R., and Y. Kloog, *Farnesyl Derivatives of Rigid Carboxylic acids—Inhibitors of Ras-dependent Cell Growth,* 38 J. Med. Chem. 1262–1272 (1995)("Marciano et al."), each the entirety of which is incorporated herein by reference.) Because FTS does not inhibit farnesylation or methylation of Ras in intact cells (Marom et al.), and because Ras farnesylation is absolutely required for membrane anchorage (Marciano et al.)(See also: Casey, P. J., Solski, P A., Der, C. J., and J. E. Buss, *p21 ras is modified by a farnesyl Isoprenoid* 86 Proc. Natl. Acad. Sci. USA 8323–8327 (1989)("Casey et al."); James, G. L., Goldstein, J. L., Brown, M. S., Rawson, T. E., Somers, T. C., McDowell, R. S, Crowley, C. W., Lucas, B. K., Levinson, A. D., and J. C. Masters Jr., *Benzodiazepine Peptido-mimetics: Potent Inhibitors of Ras Farnesylation in Animal Cells,* 260 Science 1937–1942 (1993)("James et al."); Kato, K, Cox, A. D., Hisaka, M. M., Graham, S. M., Buss. J. E., and C J. Der,*Isoprenoid Addition to Ras Protein is the Critical Modification for its Membrane Association and Transforming Activity,* 89 Proc. Natl. Acad. Sci. USA 6403–6407 (1992) ("Kato et al."); Hancock, J. F., Magee, A. I, Childs, J. E., and C. J. Marshall, *All Ras Proteins are Polyisoprenylated but only some are palmitoylated,* 57 Cell 1167–1177 (1989) ("Hancock I et al."); and Hancock, J. F., Caldwallader, K., Pterson, H., and C. J. Marshall, *A CAAX or a CAAL Motif and a Second Signal are Sufficient for Plasma Membrane Targeting of Ras Proteins,* 10 EMBO J. 4033–4039 (1991) ("Hancock II et al.") each the entirety of which is incorporated herein by reference.), we hypothesized that FTS might act on Ras anchorage sites in the cell membrane. The effects of FTS on Ras localization in EJ cells were examined using FTS concentrations (5–50 $\mu$M) which were shown previously to inhibit cell growth without producing cytotoxicity (Marom et al., Marciano et al., supra).

General Methods

The following methodologies were utilized in these reduction-to-practice/proof-of-principle experiments:

Immunoprecipitation and Immunoblotting of Ras

Ha-Ras transformed Rat1 cells (EJ cells) were plated at a density of $4 \times 10^6$ cells/10 cm dish. After 3 hr the cells were treated for 15 hr (dose response) or for 2, 6, 12, or 24 hr (time course) with FTS (0–50 $\mu$M, dose response) or (25 $\mu$M, time course) or (0.1% DMSO, control). The cells were then detached from the dishes and washed in phosphate-buffered saline (PBS). All the subsequent procedures were carried out at 4° C. The cell pellets were homogenized in 750 ml of homogenization buffer 20 mM Tris-HCl, pH=7.6) leupeptine (5 $\mu$g/ml), pepstatine (5 $\mu$g/ml), benzamidine (1 $\mu$M), phenylmethyl-sulphonyl fluoride (1 mM), aprotinine (5 units/ml), and $MgCl_2$ (10 mM). Total cell membranes ($P_{100}$) and cytosol ($S_{100}$) were obtained by a 100,000×g centrifugation step (30 min). Following resuspension of the $P_{100}$ in 750 $\mu$l of homogenization buffer, both $S_{100}$ and $P_{100}$ received 75 $\mu$l of 10×immunoprecipitation buffer (100 mM Tris-HCl, pH=7.5, 1.5 M NaCl, 10% Triton X-100). Samples were frozen for 1 hr at −70° C. and then thawed. Insoluble material was removed by a 10 min 10,000×g spin and the clear supernatant was used for immunoprecipitation. Samples containing 500 $\mu$g protein of $P_{100}$ and the equivalent amount of $S_{100}$ protein, were incubated for 12 hr with 2 $\mu$g of Y13-259 antibodies coupled to agarose bends (Oncogene Science). The beads were then precipitated and washed four times with 1 ml of immunoprecipitation buffer, twice with 1 ml of 20 mM Tris-HCl, pH=7.6, and then resuspended in 20 $\mu$l of SDS-sample buffer. Proteins were then separated by 12.5% SDS-PAGE (mini gels) and blotted onto nitrocellulose paper. The paper was blocked with 10% skimmed milk in tris-buffered saline and then incubated for 7 hr with rabbit anti-Ras serum diluted 1:1000 with tris buffered saline containing 10 mg/ml bovine serum albumin and 0.05% tween-20 (anti-Ras antiserum was prepared by immunizing rabbits with recombinant human-Ha-Ras (Marom et al.). Immunoblots were then incubated for 1 hr with 1:5000 dilution of goat anti-rabbit IgG-horseradish peroxidase (HRP) conjugate (Sigma) and developed by exposing to ECL.

In experiments where the total amount of Ras was estimated, the cells were homogenized as detailed above and samples of the total cell-homogenate (15 $\mu$g protein) were loaded onto the gel. For immunoblotting, we have also used the pan-Ras Ab (Calbiochem) at a 1:2000 dilution, and anti-mouse IgG-HRP at a 1:7500 dilution. To develop, the blots were exposed to ECL. The same immunoblotting procedure was also used in the cell-free system experiments.

Immunoblotting of G$\beta\gamma$

The level of G protein $\beta$ (G$\beta$) was determined in membranes of EJ cells that were grown in the absence and in the presence of FTS in the same conditions that were used for Ras detection. A sample of 25 $\mu$g membrane proteins were separated by SDS-PAGE (12.5%), and blotted to nitrocellulose paper. Immunoblots were performed by using rabbit anti G$\beta$ antibodies (dilution of 1:1000) as a first antibody and goat anti rabbit IgG HRP (Sigma) as a second antibody (dilution of 1:5000). To develop, the blots were exposed to ECL.

Degradation of Ras

Degradation of Ras was determined by pulse chase experiments. EJ cells were plated at a density of $3 \times 10^6$ cells/10 cm dish in DMEM with 10% FBS. One day after plating, the cells were starved for serum and methionine and pulsed with $^{35}$S cysteine/methionine (100 $\mu$Ci/ml (NEN)) for 12 hr. Chase was done by removal of the pulse medium and addition of fresh medium (containing methionine and serum) with 25 $\mu$M FTS or with 0.1% DMSO (control) for 6, 12, 24 hr. The cells were detached and washed as described,supra, and homogenized in 500 $\mu$l of homogenization buffer. The total homogenate received 50 $\mu$l of 10×immunoprecipitation buffer. The samples were frozen for 1 hr at −70° C. and then thawed. Insoluble material was removed by a 10 min 10,000×g spin and the supernatants (600 $\mu$g protein) were prepared by a 1-hour incubation with 2 $\mu$g of naive rat IgG and 40 $\mu$l of 10 protein G agarose in a total volume of 500 $\mu$l of immunoprecipitation buffer. The prepared samples of protein were immunoprecipitated as described supra. Proteins were separated by 12.5% SDS-PAGE (mini gels), stained, destained, and dried. The dried gels were exposed to X-ray film for 12 hr.

Results

Figure 3A:
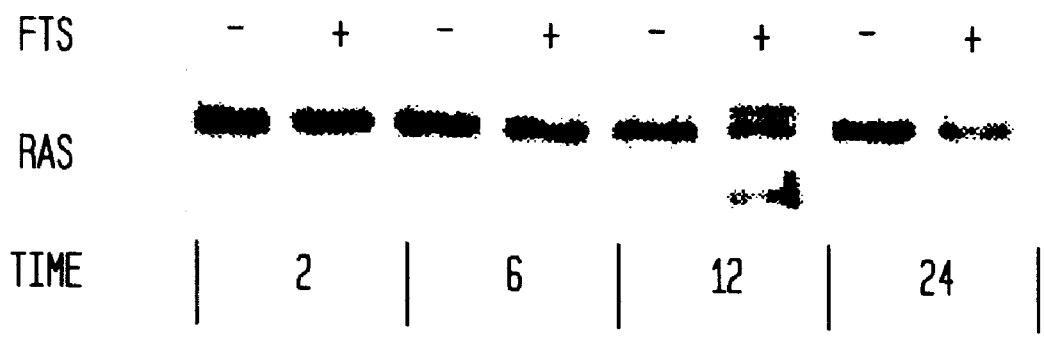
Figure 3B:
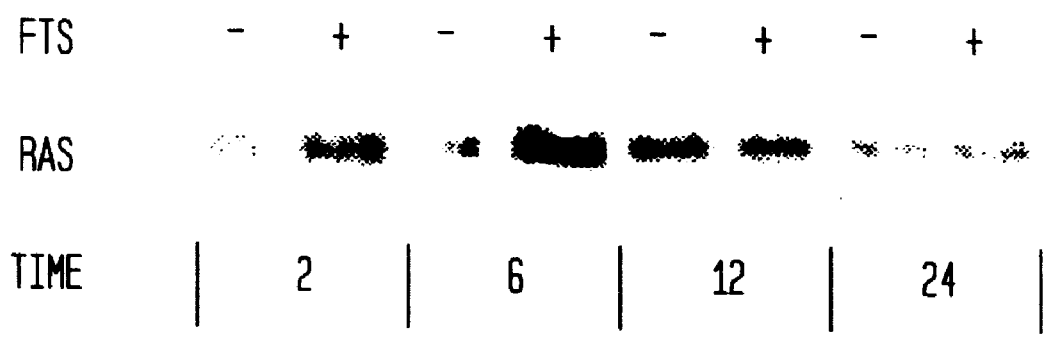
Figure 3C:
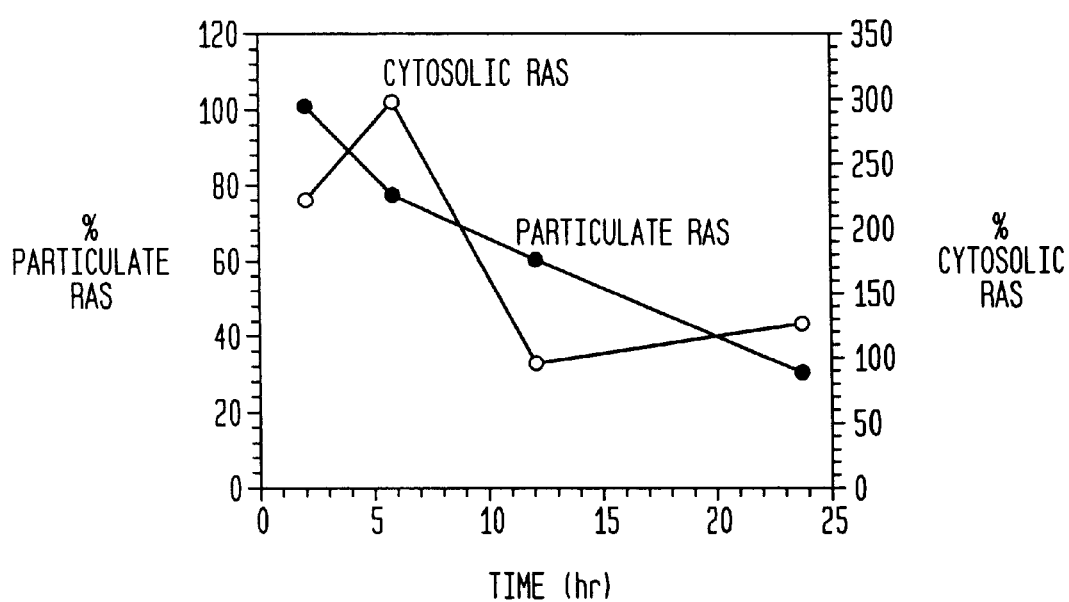

FIG. 3 shows the results of a typical experiment demonstrating the dislodging of Ras in EJ cells by FTS, where the effect of FTS is measured as a function of time. Here, EJ cells were plated at a density of $4 \times 10^6$ cells/10 cm dish. The plated cells were cultured for 3 hours and then received new media containing 0.1% DMSO with or without 25 µM FTS. The cells were further cultured for 2, 4, 12, or 24 hours before harvesting and fractionation into particulate and cytosolic fractions. Ras proteins were immunoprecipitated from the fractions, subjected to SDS-PAGE, immunoblotted and developed with ECL as described in the methods, supra. The density of the bands produced from the particulate fraction (FIG. 3A) and the cytosolic fraction (FIG. 3B) was measured with a scanning densitometer. The data obtained from the densitometric analysis are presented in FIG. 3C as the ratio of values of test (FTS treated) over control (DMSO only) cells. The mean values of three separate experiments are shown.

FTS (25 µM) caused a time-dependent decrease in the amount of Ras in the particulate fraction (FIG. 3A). The decrease was apparent after 6 hours, increased at 12 hours, and appeared to reach a maximum value at 24 hours. Densitometric analysis of data obtained in 3 separate experiments indicated that after 24 hours FTS caused an 80% decrease in the amount of particulate Ras versus control levels (FIGS. 3A & 3C). As shown in FIGS. 3B & 3C, the amount of Ras increased in the cytosol of the cells. A significant increase in cytosolic Ras occurs 2 to 6 hours after exposure to FTS then falls off precipitously thereafter. These results together with the observed decrease in particulate Ras suggest that FTS dislodges Ras from the membrane. The dislodged protein does not appear to accumulate in the cytosol, however. Instead, the increase in cytosolic Ras is transient. As the data in FIGS. 3A, 3B and 3C show, FTS ultimately causes a marked decline in both particulate and cytosolic Ras. The above results suggest that Ras is dislodged from the plasma membrane by FTS and then degraded.

Figure 4A:
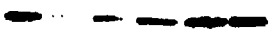
Figure 4C:
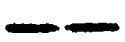
Figure 4D:
Figure 4B:
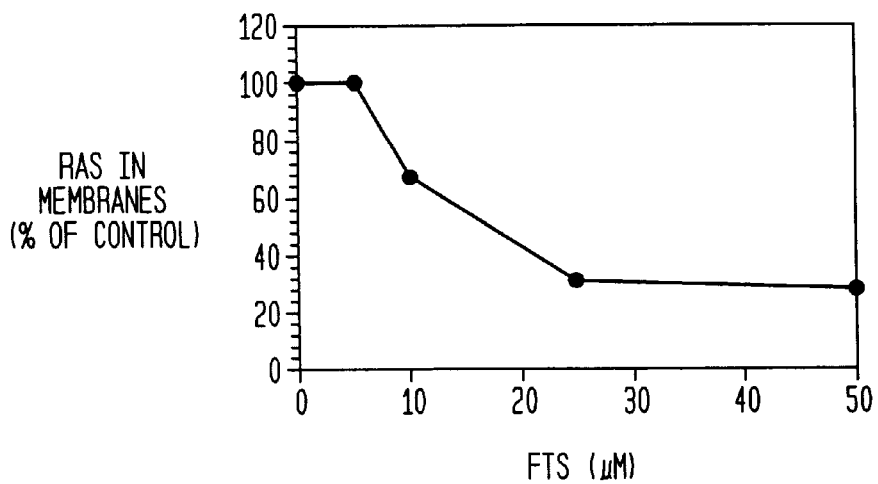

Referring to FIGS. 4A and 4B, the effect of FTS in dislodging Ras from EJ cell membranes was investigated for dose dependence. Here, Ras protein concentration was determined in the particulate fraction of EJ cells that were exposed to the indicated concentrations of FTS (0–50 µM) and AFC (50 µM) for 15 hours as detailed for FIG. 3, supra. The densitometric analysis of the immunoblot bands shown in FIG. 4A are presented in FIG. 4B as mean % of control of three experiments. As shown in FIG. 4B, the EC5O was about 10 µM. This EC5O value is comparable to the estimated EC5O for inhibition of EJ cell growth by FTS (Marom et al., Marciano et al).

Figure 5A:
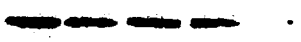

If Ras is degraded after it is dislodged, total cellular Ras should fall after FTS treatment. To investigate this, EJ cells were incubated for 15 hours, with various concentrations of FTS as detailed in FIG. 3, supra, then homogenized and total cell Ras measured by immunoblot assay. Scanned immunoblot bands of a typical experiment are shown in FIG. 5A. FTS caused a dose dependent decrease in the total amount of Ras in treated EJ cells. Densitometric analysis of data, such as that of FIG. 5A, is presented in FIG. 5B as the mean percent of control of 3 experiments. The EC5O was 15 µM (FIG. 5B), which is similar to that determined for the effect of FTS on particulate Ras.

Figure 5C:
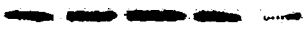
Figure 5B:
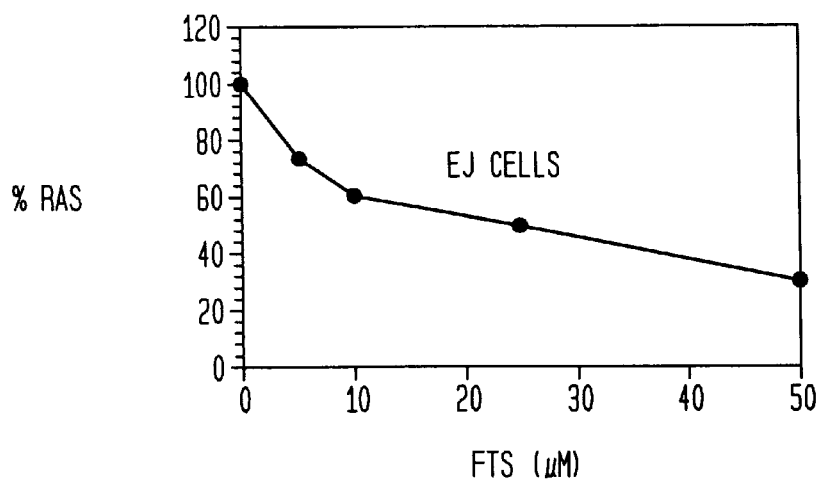
Figure 5D:
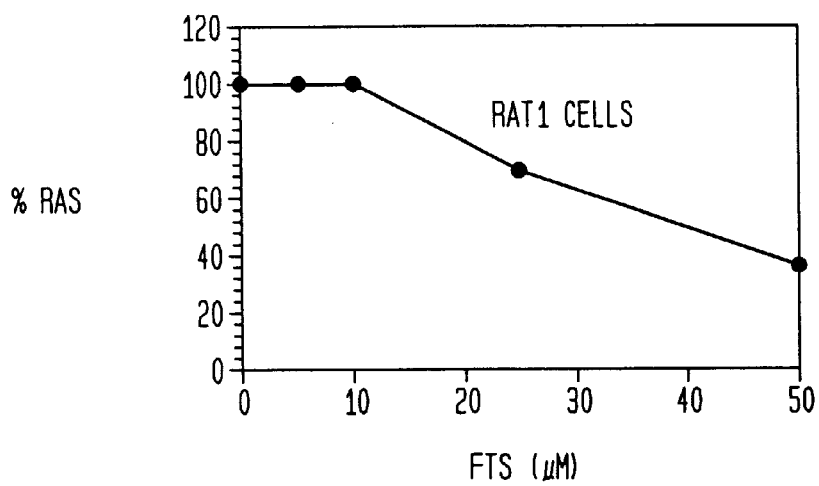

The effect of FTS on total Ras in Rat1 cells (Rat1 cells have normal rather than oncogenic Ras) was also examined using the same procedures and conditions as that used for EJ cells in FIGS. 5A & 5B. There was a significant decrease in Ras (FIGS. 5C,5D), but the dose response curve in Rat 1 cells (FIGS. 5C,5D) is shifted to the right compared to the dose response curve in EJ cells (FIGS. 5A, 5B). Similarly, as shown in FIG. 4D, FTS (50 µM) caused a decrease in particulate Ras in Rat 1 just as it did in EJ cells. However, dislodging normal Ras in Rat1 cells required 50 µM FTS whereas the oncogenic Ras found in EJ cell is dislodged at lower concentrations of the drug (FIG. 5A). Thus, FTS may have some selectivity towards the activated forms of Ras. This may account for the fact that FTS is not toxic at doses that inhibit the growth of Ras dependent cells and tumors (see toxicology section below.)

The possibility that FTS renders Ras proteins more susceptible to degradation was tested in pulse-chase experiments. EJ cells were labeled with $^{35}$S-cysteine/methionine for 12 hours, then chased for various periods of time with unlabeled cysteine/methionine. FTS was added at the beginning of the chase period. Ras proteins were immunoprecipitated from the cell lysates, separated by SDS-PAGE, and measured by autoradiography.

Figure 6A:
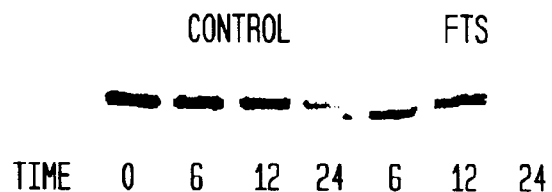
FIG. 6a demonstrates, by pulse chase, the time kinetics of FTS effect on total Ras in EJ cells.
Figure 6B:
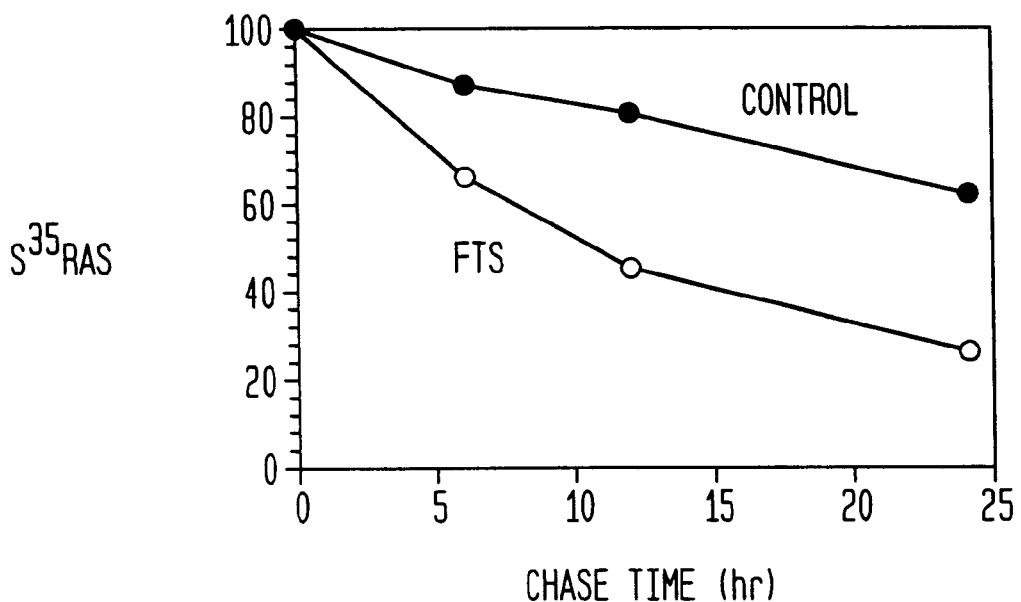

Referring to FIGS. 6A & B, EJ cells were plated at a density of $3 \times 10^6$ cells/10 cm dish. After one day cells were pulsed with $^{35}$S-cys/met (200 µCi/ml) in serum free medium without methionine for 12 hr and then chased with serum free medium in the absence or presence of FTS (25 µM) for 0–24 hours. Ras proteins were immunoprecipitated in cell homogenates standardized to 600 µg total protein. The immunoprecipitated proteins were separated by SDS-PAGE (12.5% gel), stained, destained and dried. The dried gels were exposed to X-ray film and photographed. A scan of the photograph is shown in FIG. 6A. Densitometric analysis of the data as shown in panel A, is presented as the ratio of FTS treated values over values in control cells. The Mean value of three separate experiments are shown in FIG. 6B.

Results of a typical experiment (FIG. 6A) indicate that in control EJ cells Ras degradation is relatively slow. The estimated half life of Ras in untreated cells, in these experiments, is 27 hours (n=4) (FIG. 6B). These results are consistent with earlier studies. The rate of Ras degradation in FTS treated cells was far higher (FIGS. 6A, 6B) than that of non-treated cells. The estimated half life of Ras in the presence of 25 µM FTS was 10 hours (n=4).

Our data show that FTS causes a time- and dose-dependent decrease in membrane-bound Ras. This is accompanied by a transient increase in cytosolic Ras, accelerated degradation of Ras, and a decrease in the total amount of cellular Ras. Previous studies of pharmacological and molecular reagents have not shown such effects on Ras in intact cells. The results described support the hypothesis that FTS dislodges Ras from membrane anchorage sites and that dislodged Ras is susceptible to proteolytic degradation.

While P21 Ras is lost from cell membranes and gained by the cytosol, slowly migrating (i.e. immature) forms of Ras were not detected there following treatment with FTS. This is consistent with the fact that FTS seems to have no effect on Ras maturation (Marom et al.) because inhibition of Ras farnesylation would have caused a slowly migrating form of Ras to accumulate in the cytosol (Casey et al., James et al., and Kato et al.).

The accelerated rate of Ras degradation elicited by FTS was not a phenomenon that could have been predicted or anticipated. Ras once dislodged from its membrane binding sites, could have remained associated (in a nonspecific way) with the membrane or could have formed a long-lasting complex with a cytosolic protein as Rac does with Rho-GDI. The transient appearance of Ras in the cytosol following treatment of cells with FTS suggests that released Ras does not form a stable intracellular complex. Furthermore, our data indicate that a different mechanism may be responsible for degradation of unprocessed versus fully processed farnesylated Ras. This seems reasonable it is the action of the mature protein that should be terminated when it is no longer needed.

The ability of FTS to dislodge Ras is not shared by other farnesyl derivatives. For example, N-acetylfarnesyl-cysteine (AFC) is ineffective in inhibiting the growth of Ras-transformed cells, although it does enter cells readily (Volker et al., *Effects of Farnysylacysteine Analogs on Protein Carboxyl Methylation and Signal Transduction*, 266 J Biol Chem 21515–21522 (1991) the entirety of which is herein incorporated by reference) ("Volker et al."). As shown in FIG. 4A, AFC did not affect Ras membrane localization in EJ cells either.

That FTS targets Ras and not other lipid-anchored proteins is shown by studies of the distribution of subunits of the receptor-linked trimeric G-proteins. Specifically, we looked at the Gβ subunit which is tightly associated with the prenylated Gγ subunit of the trimer (Neer, E. J., *Heterotrimeric G-proteins Organizers of Transmembrane Signals*, 80 Cell 249–257(1995)("Neer") the entirety of which is herein incorporated by reference). As shown in FIG. 4C, FTS did not reduce the amount of Gβ associated with EJ cell membranes. Thus, although FTS shows some specificity for Ras, the results do not exclude the possibility that FTS may affect other membrane proteins, including Ras-like proteins, We believe that the best explanation for the data summarized to this point is the existence of specific Ras binding sites in the plasma membrane. In favor of this are the observations that Ras binds to the plasma membrane but not other cellular membranes (Cox, et. al., *Specific Isoprenoid Modification is Required for Function of Normal, but Not Oncogenic Ras Protein*, 12 Mol Cell Biol 260–2615 (1992) ("Cox I, et. al."); Cox, et al., *Protein Prenylation: More Than Just Glue*, 4 Cur Opin in Cell Biol 1008–1016 (1992) ("Cox I, et al.") each the entirety of which is herein incorporated by reference), and that geranylgeranyl forms of Ras distribute differently than do farnesyl forms of the protein (Hancock et al., *CAAX or a CAAL Motif and a Second Signal are Sufficient for Plasma Membrane Targeting of Ras Proteins*, 10 EMBO J. 4033–4039 (1991) ("Hancock III") the entirety of which is herein incorporated by reference). The relatively low concentrations of FTS (<25 µM) required to dislodge Ras from cell membranes, the relatively narrow concentration range that will produce maximal displacement (10–50 µM) the specificity of FTS and certain related compounds in producing this effect, and the lack of any effect on G-protein subunits are also consistent with the existence of specific anchorage sites, (i.e., distinct protein receptors or a rather unique lipid environment) which have a lower affinity for oncogenic than normal Ras.

High Throughput Screen for Drugs that Displace Ras from its Anchor in Cell Membranes The cell-free assay is utilized in these next experiments; i.e. the effect of FTS on Ras in isolated membranes was investigated. Briefly, we used EJ cell membranes (total particulate fraction) prepared in homogenization buffer (10 mM Tris-HCl, pH 8.5, 0.32 M sucrose) with protease inhibitors. The membranes were stored in aliquot at –70° C. and thawed prior to use. In a standard assay, membranes containing 15 µg of protein are incubated in a total volume of 100 µl of homogenization buffer with or without drug for 60 min at 37° C. The drugs are prepared freshly in 100% DMSO, and diluted with 50 mM Tris-HCl pH 8.5 to yield 5× drug concentration in 10% DMSO. It is important to prepare these solutions at room temperature, otherwise the drugs may precipitate. The drug solutions (20 µl) are pipetted into the assay tubes, the membrane/buffer mixtures (80 µl) are quickly added, the tubes are gently mixed, and the tubes are transferred to a 37° C. shaking water bath. The reactions are stopped by addition of 900 µl of cold homogenization buffer (without sucrose) containing 10 µg BSA. Following a 5 min incubation at room temperature, the membranes are pelleted by centrifugation in a benchtop microfuge (14,000 rpm). The supernatants are removed and the pellets are subjected to mini-SDS-PAGE followed by Immunoblotting (pan anti-Ras antibodies) and ECL assays. These assays are detailed infra. It is considered preferable to perform the reactions at 25–37° C. and to use relatively small amounts of membrane protein in the assay. Another preference is to dilute the membranes in a solution containing BSA at the end of the reaction period.

Figure 7A:
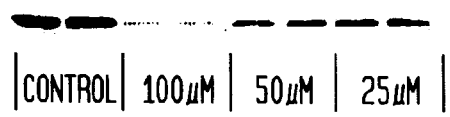
Figure 7B:
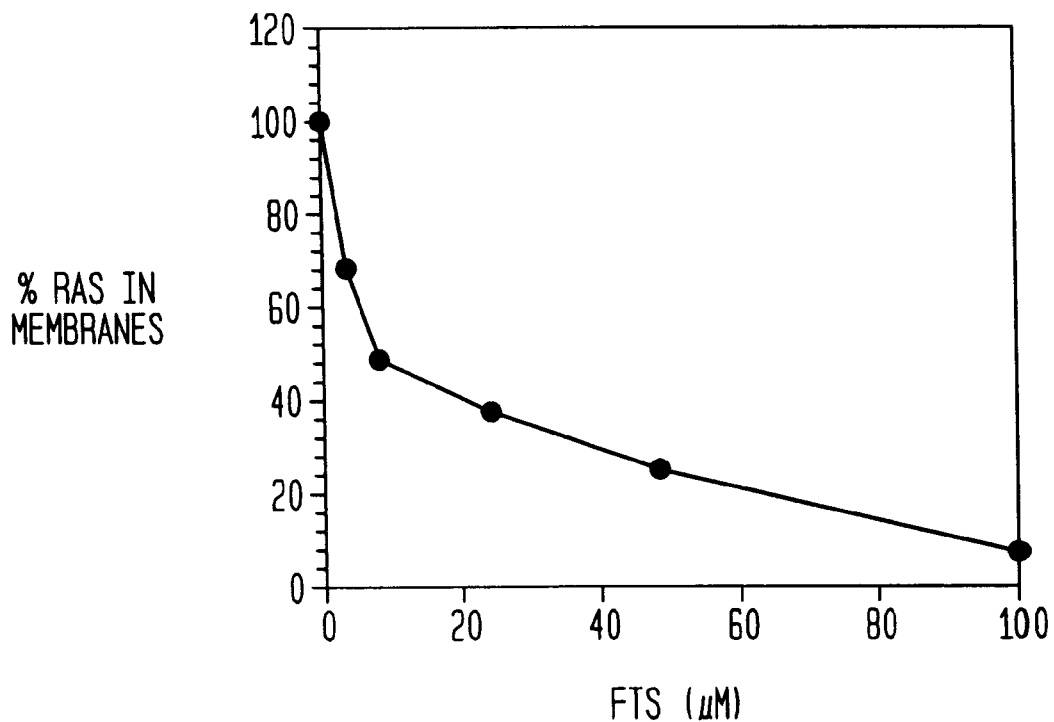

FIGS. 7A and B show that Ras was dislodged from membranes by FTS in a dose dependent manner. The drug seemed quite potent at doses as low as 10 µM (FIG. 7B). Note that the $EC_{50}$ FTS dislodging of Ras from isolated membranes was 10–15 µM (FIG. 7B), a value reasonably similar to that required to dislodge Ras in intact cells.

Figure 8:
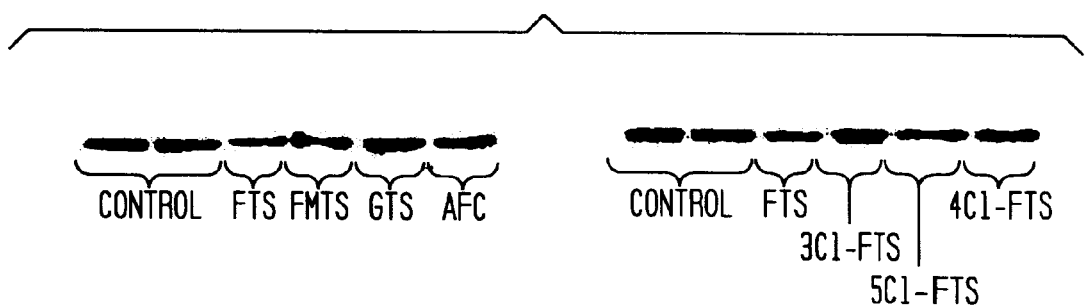
FIG. 8 are immunoblots of the effect of various compounds on the anchorage oncogenic Ras from isolated EJ cell membranes (cell free assay).

In a second set of experiments we examined the ability of compounds related to FTS in structure to dislodge Ras from isolated membrane. We studied AFC and a number of farnesyl derivatives of rigid carboxylic acids. The results are shown in FIG. 8. To avoid nonspecific effects that might be seen at high concentrations of the compounds, we tested each agent at a 10 µM concentration. FTS, AFC, carboxymethyl FTS (FMTS), 5-Cl-FTS, 3-Cl-FTS, 4-Cl-FTS, and geranyl thiosalicylic acid (GTS) were examined. The rank order of potency of the compounds appears to be FTS>5-Cl-FTS>4-Cl-FTS>3-Cl-FTS=FMTS=GTS=AFC. The last 4 compounds of this group did not dislodge Ras under the conditions used (FIG. 8 and Table 4). Table 4 also compares the doses of the various compounds required to inhibit EJ cell growth. There is a fair correlation between the rank order of potency of the various compounds in the cell free assay and their actionson intact cells.

Adaptability. Versatility, and Range of Usefulness

The employment of the Anchor Disruption Assay of the present invention includes a wide range of assay variations based on the theme of:

an assay material being generated that includes at least one target lipoprotein anchored in membrane (isolated membrane, whole cell, or living organism), incubating the substance to be tested with the membrane-lipoprotein target (in a test tube, a tissue culture well, or by injection), detecting the proportion of target that has dissociated from the membrane.

The following six embodiments are described as examples of variations on the theme which may be employed and are considered to be within the scope of this invention.

Embodiment I

Figure 9:
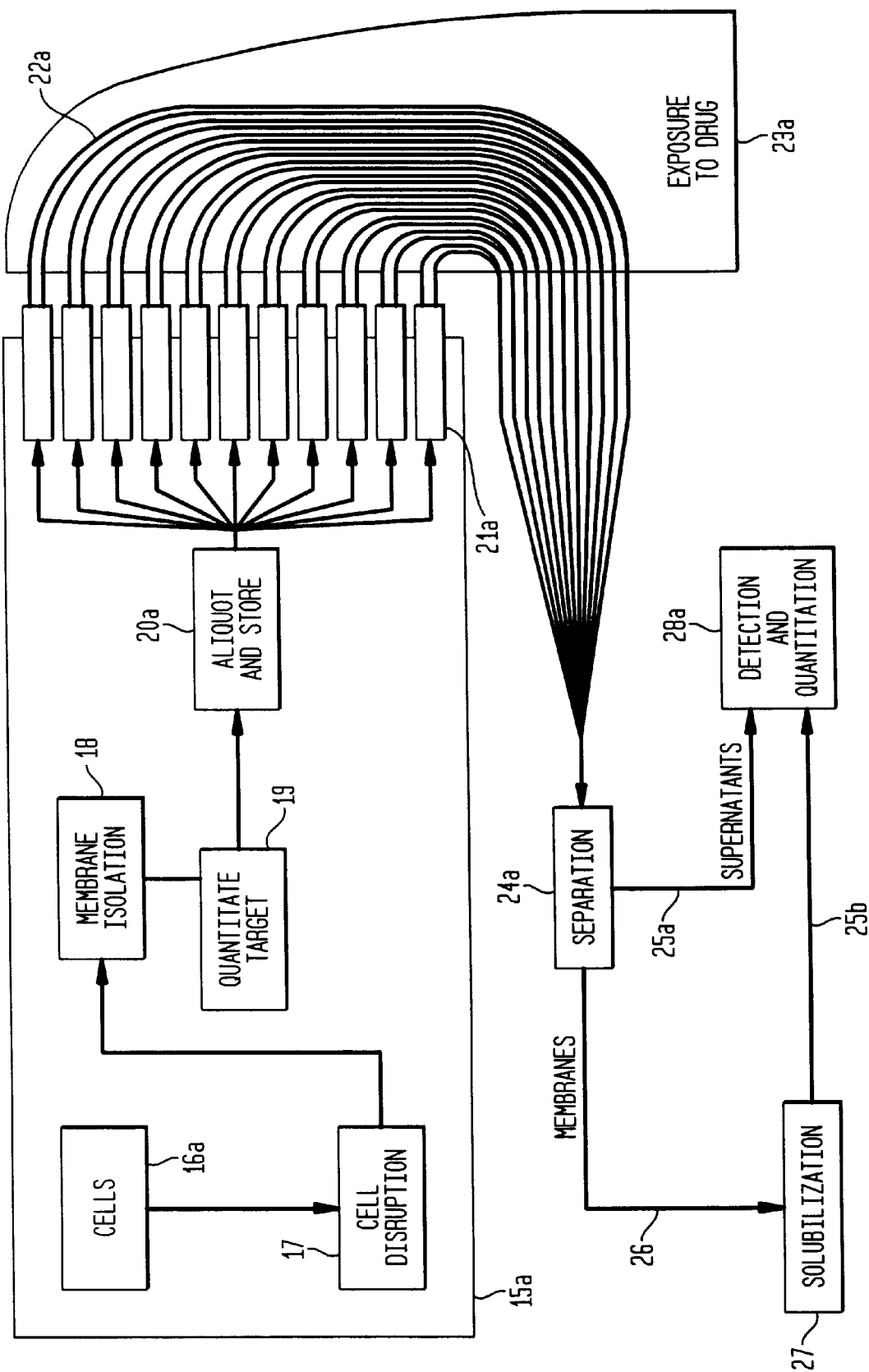
FIG. 9 is a flow chart diagraming the cell free assay for effect of drug on target. such as oncogenic Ras, anchored to membrane in autologous cells using an immunologic tag of embodiment I.

A Cell Free Assay for Effect of Drug on Target, Such as Oncogenic Ras, Anchored to Membrane in Autologous Cells Using an Immunologic Tag Referring to FIG. 9, an assay material preparation procedure 15a is performed in advance to generate the appropriate purified membranes having a standardized concentration of target protein anchored therein. Since this embodiment is an example of an autologous target, the starting material is a culture of cells 16a, that express the target constitutively.

The example used in the proof of principle section, supra, of oncogenic ras in EJ cells is typical of a constitutively expressed target in an autologous cell line. The cell line is grown to a large quantity for the purpose of standardization and the cells are collected and washed in a lysing buffer containing protease inhibitors to stay target degradation. Cells thus harvested are subjected to a cell disruption procedure 17 followed by a membrane isolation procedure 18 each as described, supra.

A small sample of purified membranes from isolation procedure 18 is assayed in a quantitate target step 19 to determine target protein concentration in the total remaining output. Optimally, the same quantitation procedure is used at quantitate target step 19 as will be used to assay the endpoint after drug exposure. Here in embodiment I, the final assay exemplifies the use of a quantitative immunoassay so the same immunoassay is used at quantitate target step 19. Once the target concentration is determined it is adjusted to a standard concentration in an aliquot. and store step 20a the output of which is a multiplicity of membrane-target aliquot 21a. Membrane-target aliquot 21a are stored frozen until ready for use.

Using the aliquoted starting material from assay material preparation procedure 15a the next major procedural component of the assay, an exposure to drug procedure 23a, consists of a multiplicity of drug incubations 22a each involving, placing a composition to be tested for a specified period of time, diluted in a solvent carrier at a known concentration, in one aliquot 21a. Exposure to drug procedure 23a is depicted here as a sample of the various concentrations, controls, incubation times, etc. needed to screen a particular compound for its potential target protein membrane anchorage disruption effect. Each drug incubation 22a is rendered, in FIG. 9, as a gradually disintegrating black-to broken line to depict the drug effect of removing the target from its anchor site at the membrane.

Exposure to drug procedure 23a is ended by a separation procedure 24a that separates the membranes in each aliquot 21a into a membrane fraction and a supernatant. Here, separation procedure 24a is a simple centrifugation. removal of the supernatant to a first soluble fraction 25a leaving a membrane pellet 26, washing membrane pellet 26 with a small amount of wash buffer, and removing the wash to combine with first soluble fraction 25a. Membrane pellet 26 is subjected to a detergent solubilization 27 which solubilizes the remaining target into a second soluble fraction 25b.

Soluble fractions 23a & b are assayed for the presence of target in detection and quantitation step 28a. Here, since no labeling step is performed during assay material preparation procedure 15a, the detection is direct, utilizing the inherent immunologic specificity of the target. A quantitative immunoassay such as RIA or rocket immunoelectrophoresis is most appropriate for detection and quantitation step 28a. Note that membranes being assayed in quantitate target step 19 of assay material preparation procedure 15a will include both solubilization step 27 and detection and quantitation step 28a.

The output of detection and quantitation step 28a will be a determination of the relative proportion of target that has moved from the membrane to the supernatant as a result of the incubation with drug. This determination will be calculated as the total target in soluble friction 25a over the total target in fractions 25a plus 25b. Standardization is accomplished by comparing the 25a plus 25b result with the input target amount in aliquot 21a determined by quantitate target step 19.

Figure 10:
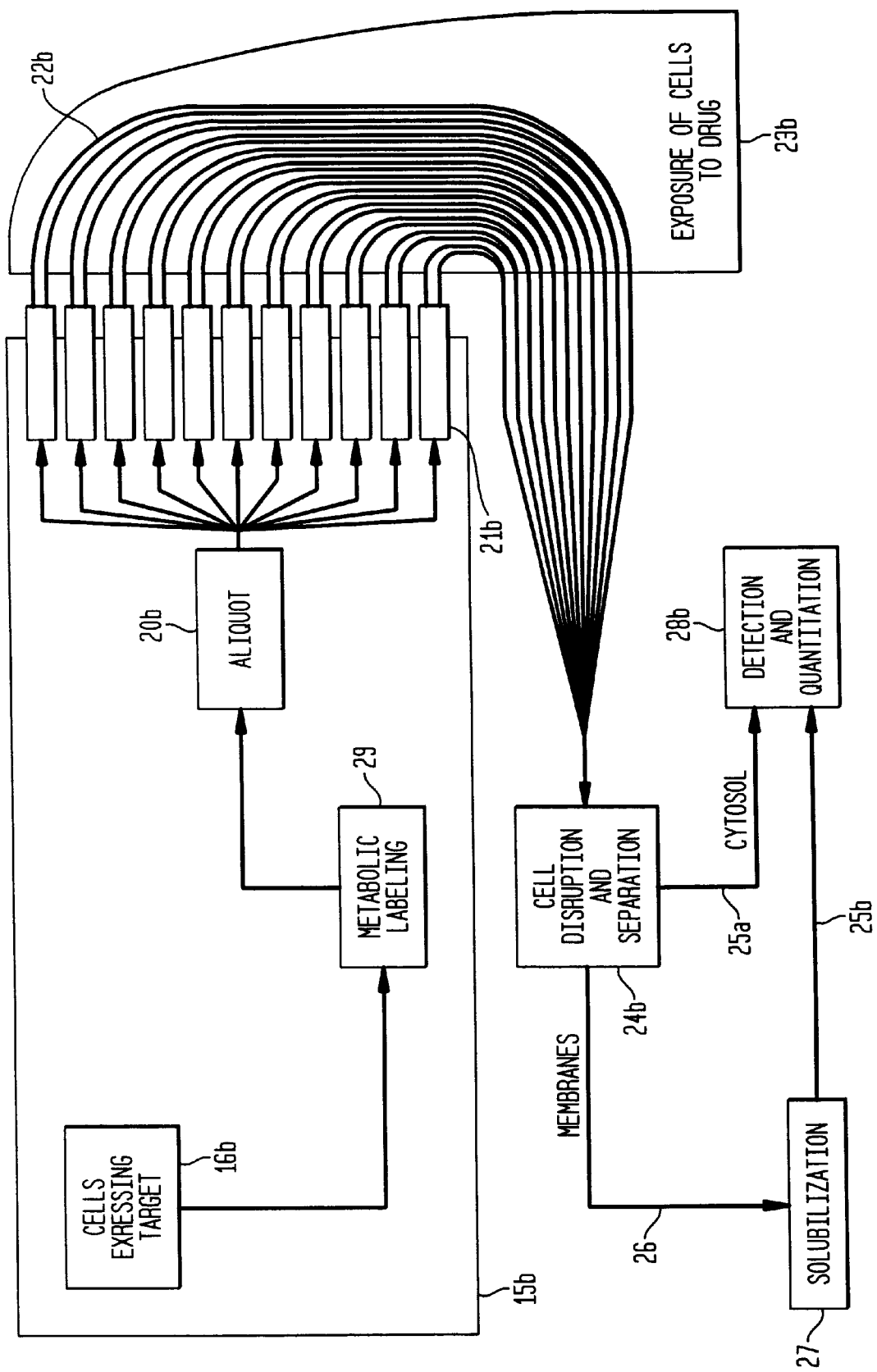
FIG. 10 is a flow chart diagraming the in vitro assay for effect of drug on target anchored to plasma membrane in autologous cells using metabolic labeling with $^{35}$S Met and Cys of embodiment II.

Embodiment II
In Vitro Assay for Effect of Drug on Target Anchored to Plasma Membrane in Autologous Cells Using Metabolic Labeling with $^{35}S$ Met and Cys Referring to FIG. 10, an assay material preparation procedure 15b is performed immediately prior to drug exposure to generate cells with freshly labelled target protein anchored therein. Since this embodiment is an example of an autologous target, the starting material is a culture of cells 16b, that express the target constitutively. The example used in the proof of principle section, supra, of oncogenic Ras in EJ cells is typical of a constitutively expressed target in an autologous cell line. The cell line is grown to a quantity needed for the assay performed immediately thereafter and a metabolic labeling procedure is performed to facilitate detection of the target at a final detection and quantitation step 28b. After metabolic labeling 29, the cells are collected and washed to remove excess label. The cells are adjusted to a standard cell concentration in an aliquot step 20b, the output of which is a multiplicity of in vitro membrane-target aliquot 21b.

Using the aliquoted starting material from assay material preparation procedure 15b the next major procedural component or the assay, an exposure to drug procedure 23b, consists of a multiplicity of drug incubations 22b each involving, placing a composition to be tested for a specified period of time, diluted in a solvent carrier at a known concentration, in one aliquot 21b. Exposure to drug procedure 23b is depicted here as a sample of the various concentrations, controls, incubation times, etc. needed to screen a particular compound forits potential intracellular target protein membrane anchorage disruption effect. Each drug incubation 22b is rendered, in FIG. 10, as a gradually disintegrating black-to-broken line to depict the drug effect of removing the target from its intracellular anchor site at the membrane.

Exposure to drug procedure 23b is ended by a cell disruption and membrane separation procedure 24b that disrupts the cells as in cell disruption step 17 of embodiment I, supra, then separates the disrupted cells into a membrane fraction 26 and a cytosol containing first soluble fraction 25a. Here, separation procedure 24b is a simple centrifugation, removal of the cytosol containing supernatant to first soluble fraction 25a leaving a membrane pellet, washing the membrane pellet with a small amount of wash buffer, and removing the wash to combine with first soluble fraction 25a. The cleaned membrane pellet, membrane fraction 26, is subjected to a detergent solubilization 27 which solubilizes the remaining target into a second soluble fraction 25b.

Soluble fractions 25a & b are assayed for the presence of target in detection and quantitation step 28b. Here, since labeling step 29 is performed during assay material preparation procedure 15, the detection is indirect, utilizing the presence and quantity of the tag as an indicator of the presence and quantity of the target. However since the labeling is a metabolic labeling not only the target is labeled but all proteins in the cell are labelled with the tag. Therefore, the inherent immunologic specificity of the target is additionally utilized to purify the target from the other cellular proteins. A quantitative immunoassay such as rocket immunoelectrophoresis is again most appropriate for detection and quantitation step 28b. Other purification and quantitation procedures such as immunoabsorption and counting, or immunoprecipitation, PAGE, and densitometry are also useful and appropriate. The quantitative procedures are eased by the presence of the label in that the target can be detected by its tag at any point in the separation/purification process.

The output of detection and quantitation step 28b will be a determination of the relative proportion of target that has moved from the membrane to the supernatant as a result of the incubation with drug. This determination will be calculated as the total target in soluble fraction 25a over the total target in both fractions 25a plus 25b.

Figure 11:
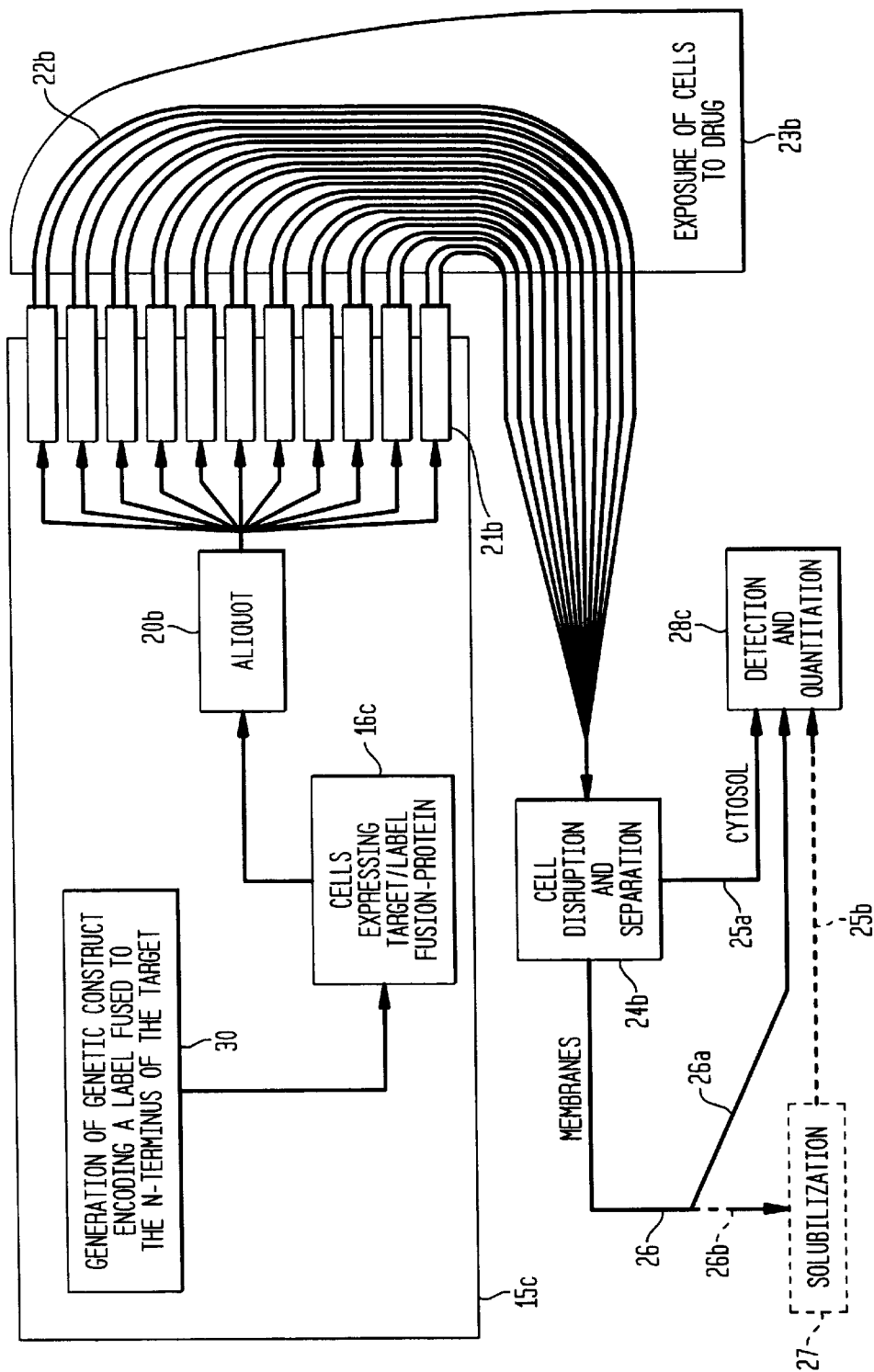
FIG. 11 is a flow chart diagraming the in vitro assay for effect of drug on target protein anchored to plasma membrane in allogeneic cells using genetic labeling with a label gene of embodiment III.

Embodiment III
In Vitro Assay for Effect of Drug on Target Protein Anchored to Plasma Membrane in Allogeneic Cells Using Genetic Labeling with a Label Gene Referring to FIG. 11, an assay material preparation procedure 15c is performed immediately prior to drug exposure to generate cells with freshly labelled target protein anchored therein. Since this embodiment is an example of an allogeneic target, the starting material is a culture of cells 16c, that do not express the target constitutively. For example, described in the proof of principle section, supra, oncogenic Ras is not found in Rat-1 cells. Initially a construct is inserted in a mammalian cell transformation vector with a strong promoter that consists of the gene encoding oncogenic Ras continued in proper reading frame by the gene for a label protein such as green fluorescent protein or luciferase. The construct is then used to transform the Rat-1 cells in a transformation procedure 30.

Cells stably expressing the target-label fusion protein are cultured as in embodiment II, supra, but are specifically and constitutively labeled and do not require metabolic labeling step 29. The cell line is grown to a quantity needed for the assay performed immediately thereafter and the cells are collected and adjusted to a standard cell concentration in an aliquot step 20b, the output of which is a multiplicity of in vitro membrane-target aliquot 21b.

As in embodiment II, supra, using the aliquoted starting material from assay material preparation procedure 15b the next major procedural component of the assay, an exposure to drug procedure 23b, consists of a multiplicity of drug incubations 22b each involving, placing a composition to be tested for a specified period of time, diluted in a solvent carrier at a known concentration, in one aliquot 21b. Exposure to drug procedure 23b is depicted here as a sample of the various concentrations, controls, incubation times, etc. needed to screen a particular compound for its potential intracellular target protein membrane anchorage disruption effect. Each drug incubation 22b is again rendered, in FIG. 11, as a gradually disintegrating black-to-broken line to depict the drug effect of removing the target from its intracellular anchor site at the membrane.

Exposure to drug procedure 23b is ended by a cell disruption and membrane separation procedure 24b that disrupts the cells as in cell disruption step 17 of embodiment I, supra, then separates the disrupted cells into a membrane fraction 26 and a cytosol containing first soluble fraction 25a. In the example here, separation procedure 24b is a simple centrifugation, removal of the cytosol containing supernatant to first soluble fraction 25a leaving a membrane pellet. Then the membrane pellet is washed, with a small amount of wash buffer. The wash is removed and combine with first soluble fraction 25a.

Since the target is specifically and exclusively labelled there is no need to purify the target from the other cellular proteins, which are unlabeled. Therefore, detergent solubilization step 27 is optional in this embodiment as indicated by the dashed lined. If chosen, the cleaned membrane pellet, membrane fraction 26b, is subjected to a detergent solubilization 27 which solubilizes the remaining target into a second soluble fraction 25b. Otherwise membrane fraction 26a is assayed directly alongside first soluble fraction 25a.

The variables that would determine whether solubilization step 27 is used may include: the type of tag (fluorescent, enzymatic, etc.), whether the presence of the membrane interferes with the detection (quenching, steric hindrance, etc.), whether the tag portion needs to be cleaved from the target portion in order to be active, etc.

Soluble fractions 25a and either 26a or 26b are assayed for the presence of target in detection and quantitation step 28c. Here, since labeling is genetically encoded when the target is transcribed and translated, the detection is direct, utilizing the presence and quantity of the tag as a 1:1 molar equivalent of the presence and quantity of the target. Additionally, since the labeling is a genetic labeling only the target is labeled, all other proteins in the cell are remain unlabelled.

The type of tag determines the detection method. For example if the tag is an enzyme such as Alk Phos or HRP then the enzymatic activity is measured in an endpoint of kinetic color development assay. On the other hand, if the tag is a light emitter, such as GFP or luciferase, then the appropriate excitation conditions are met (exposure to excitation wavelength light for GFP, presence of ATP etc. for luciferase) and the emission intensity is measured.

The output of detection and quantitation step 28c will be a determination of the relative proportion of target that has moved from the membrane to the supernatant as a result of the incubation with drug. This determination will be calculated as the total target in soluble fraction 25a over the total target in both fractions 25a plus 26a or 25b; the total target in fraction 26a or 25b over the total target in both fractions 25a plus 26a or 25b; or a variation thereof.

Embodiment IV
In Vivo Assay for Effect of Drug on Target Protein Anchored to Plasma Membrane in Allogeneic Cells Using Genetic Labeling with a Label Gene Such as GFP The presence of cells stably expressing properly anchored tagged target provides an opportunity to adapt the screening assay to simultaneously determine dosage, efficacy, clearance effects, tissue specificity, target location, and toxicity by injecting the transformed cells into appropriate animal hosts.

Figure 12:
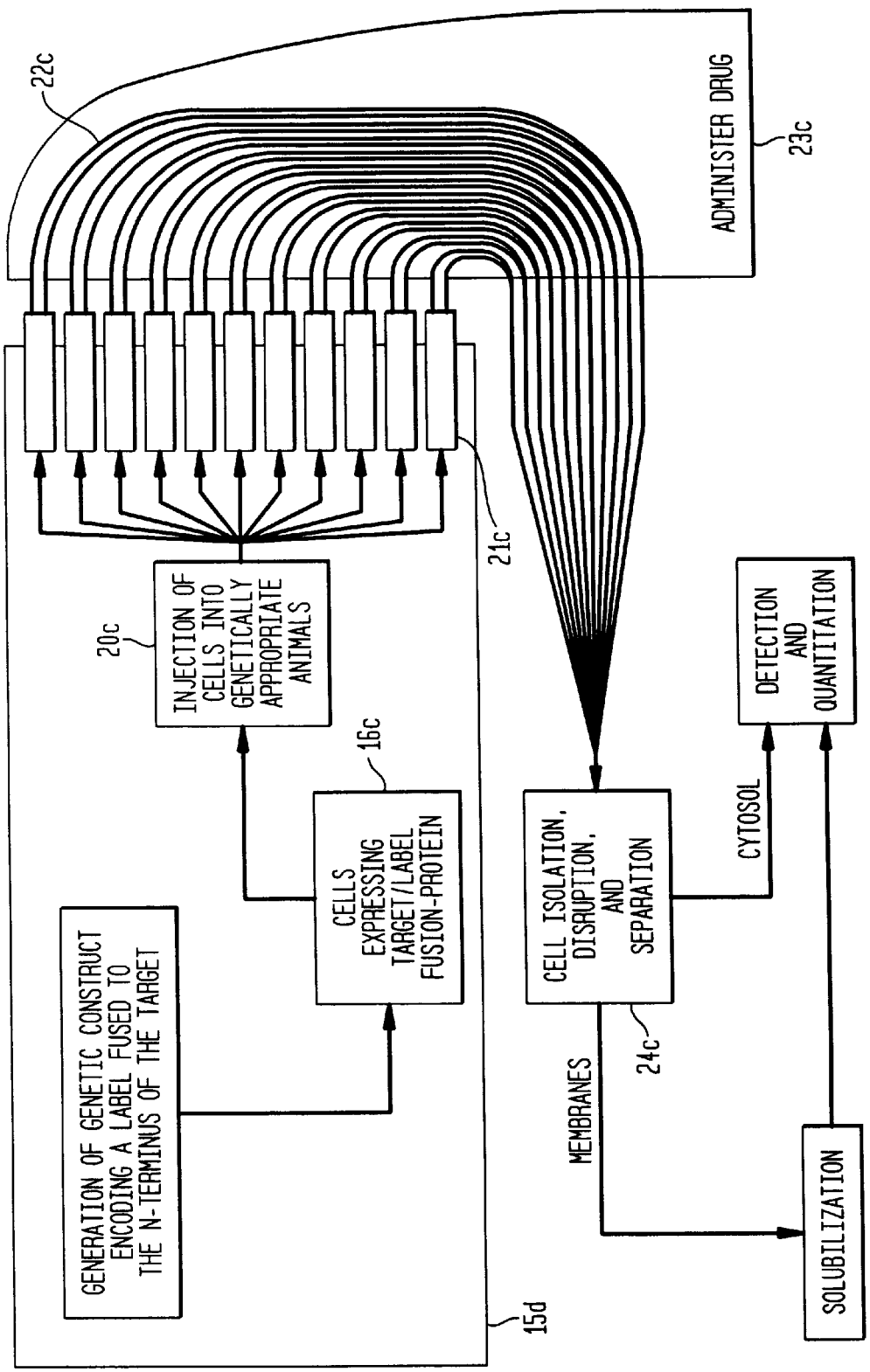
FIG. 12 is a flow chart diagraming the in vivo assay for effect of drug on target protein anchored to plasma membrane in allogeneic cells using genetic labeling with a label gene such as GFP of embodiment IV.

Referring to FIG. 12 in comparison with FIG. 11, supra, aliquot step 20b of material prep procedure 15c, where cells are aliquoted into individual assay wells or tubes, is replaced with a cell injection step 20c where the cells are aliquoted by injection into allogenetically appropriate host animals 21c. A drug administration procedure 23c includes a multiplicity of individual exposures 22c, each performed to test a dosage, route, time interval, formulation, carrier, adjuvant, etc. Each exposure 22c is given to an individual host animal 21c in this embodiment as opposed to each exposure 22b of FIG. 11 being directed to an individual culture well 21b. Additionally disruption and separation step 24b of FIG. 11 is augmented in FIG. 12 with a cell isolation component. The cell isolation component of isolation. disruption, and separation step 24c is required to retrieve the labeled target expressing cells previously injected at injection step 20c from the treated test animal 21c. Once the cells are isolated the test assay proceeds as in embodiment III, supra.

Figure 13:
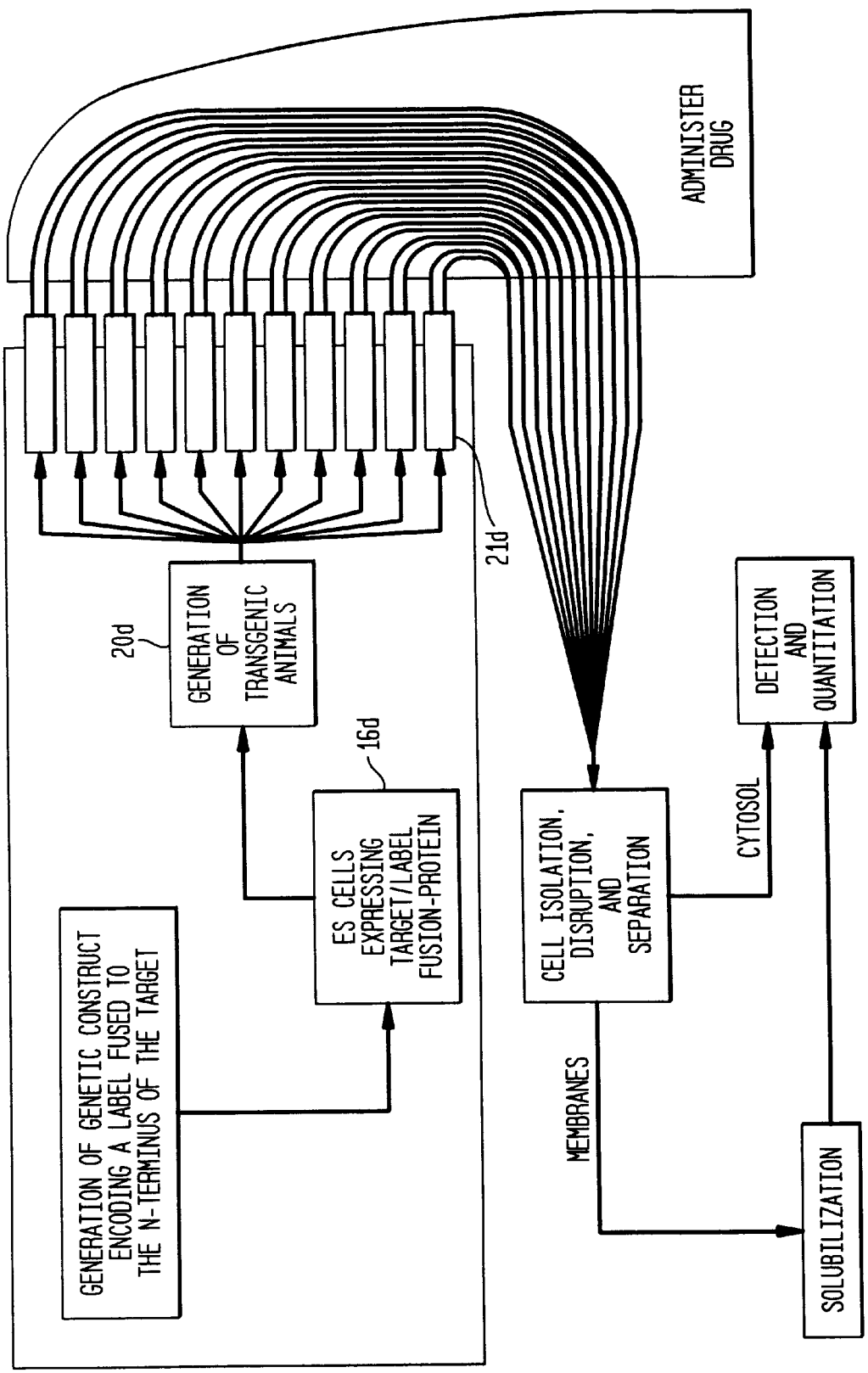
FIG. 13 is a flow chart diagraming the in vivo assay for effect of drug on target protein anchored to plasma membrane in transgenic animal cells using genetic labeling with a label gene such as GFP or luciferase of embodiment V.

Embodiment V
In Vivo Assay for Effect of Drug on Target Protein Anchored to Plasma Membrane in Transgenic Animal Cells Using Genetic Labeling with a Label Gene Such as GFP or Luciferase Referring to FIG. 13, in comparison with FIG. 12, the constructs used to generate cells 16c are instead used to transform embryonic stem cells (ES cells 16d) which are in turn utilized in the generation of transgenic animals which express the target in all cells. Alternatively, a construct with a tissue specific promoter may be used to limit the expression to specific tissues in the transgenics 21d.

Embodiment VI
In Vitro or In Vivo Assay for Effect of Drug on Synthetic Target Using Genetic Labeling with a Label Gene, Such as GFP or Luciferase, Fused to a Target Activated Reporter Gene The versatility, elegance and sophistication of the anchor disruption assay are increased with the use of synthetic targets. Such targets utilize the strategy of substituting a protein that is normally not a lipoprotein for the target by altering the gene for the protein to include the proper lipidation modification motif The strategies for utilizing this embodiment include:

1) purposely partitioning a cytosolic protein to anchor in the membrane where it normally activates, so that it becomes constitutively activated, then looking for deactivation as an indication of release from the anchor site;
2) purposely partitioning a cytosolic protein to anchor in a distant membrane sequestered from its normal activation membrane site, so that it becomes unable to be activated, then looking for activation as an indication of release from the anchor site;
3) Sequestering a nuclear transactivation element to a membrane and simultaneously make the gene that the transactivation element promotes a tag gene such as GFP or luciferase, so that the tag cannot be translated as long as the transactivator remains anchored, then looking for expression of the tag gene responsively to dislodging of the transactivator from its anchor;
4) Same as "3" except that the target is a specific transcription inhibitor so that the tag gene is constitutively expressed unless the target is dislodged; and
5) in systems where the target is a trigger protein for a well characterized activation cascade, many of the molecules that become activated by that cascade cause expression of subsequent elements, the tag gene here is given the promoter for one of those subsequently expressed elements such that dislodging of the target trigger protein will block expression of the tag gene under conditions that normally cause activation of the trigger.

For example, as incorporated by reference in the background section, Omer & Gibbs, Denhardt, supra, the CAAX prenylation motif causes the prenylation of the target at the cysteine. The specific prenylation that occurs, responsively to the identification of the X, determines the intracellular membrane to which the prenylated target partitions.

For an example of embodiment VI-1, based on the background work of T. Joneson, et al., 271 Science 810 (1966) ("Joneson"), the entirety of which is incorporated herein by reference, CAAX could be attached to Raf. This would result in its activation since it would be drawn into the membrane. When Raf is activated it activates the bfos serum response element (SRE). Several copies of the SRE are attached to a tag gene. The tag would then be constitutively expressed unless the Raf is dislodged by the test drug.

For an example of embodiment VI-2, also based on Joneson, since Raf is activated as a result of normal Ras activation or oncogenic Ras the use of the SRE-tag reporter system would indicate the activation of Raf Ydj1 heat shock protein prenylated by farnesyl protein transferase associates with the cytoplasmic side of ER and nuclear membrane. Raf is normally cytoplasmic; however, in cells where the Raf is modified with the CAAX element from the Ydj1 ("Raf$_y$") it would associate with the cytoplasmic side of ER and nuclear membrane and not be available to interact with activated Ras. Drugs could then be screened for their ability to preferentially dislodge Raf$_y$ which would then be able to interact with activated Ras thereby causing expression of the SRE-tag.

Figure 14:
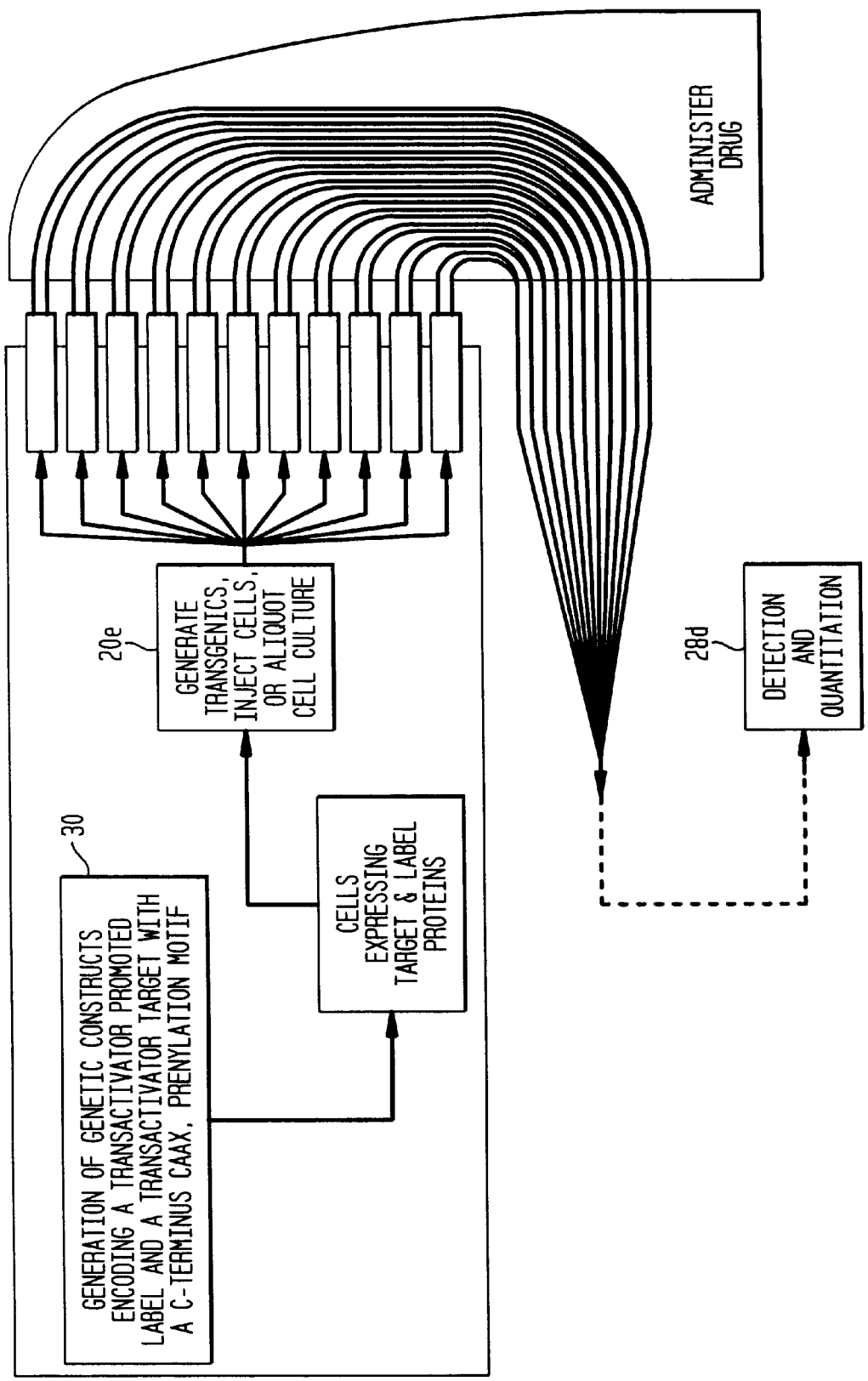
FIG. 14 is a flow chart diagraming the in vitro or in vivo assay for effect of drug on synthetic target using genetic labeling with a label gene such as GFP or luciferase, fused to a target activated reporter gene of embodiment VI.

Referring to FIG. 14, one potential advantage of using the strategies of embodiment(s) VI is the elimination of post assay processing. Once the system is in place a detection and quantitation 28d is simply accomplished by measuring cellular fluorescence intensity. The assay can be adapted at aliquot step 20e for in vitro type assays using cultured cells, in vivo assays by injecting cultured cells into animals, or in vivo by generating transgenic animals.

Figure 15:
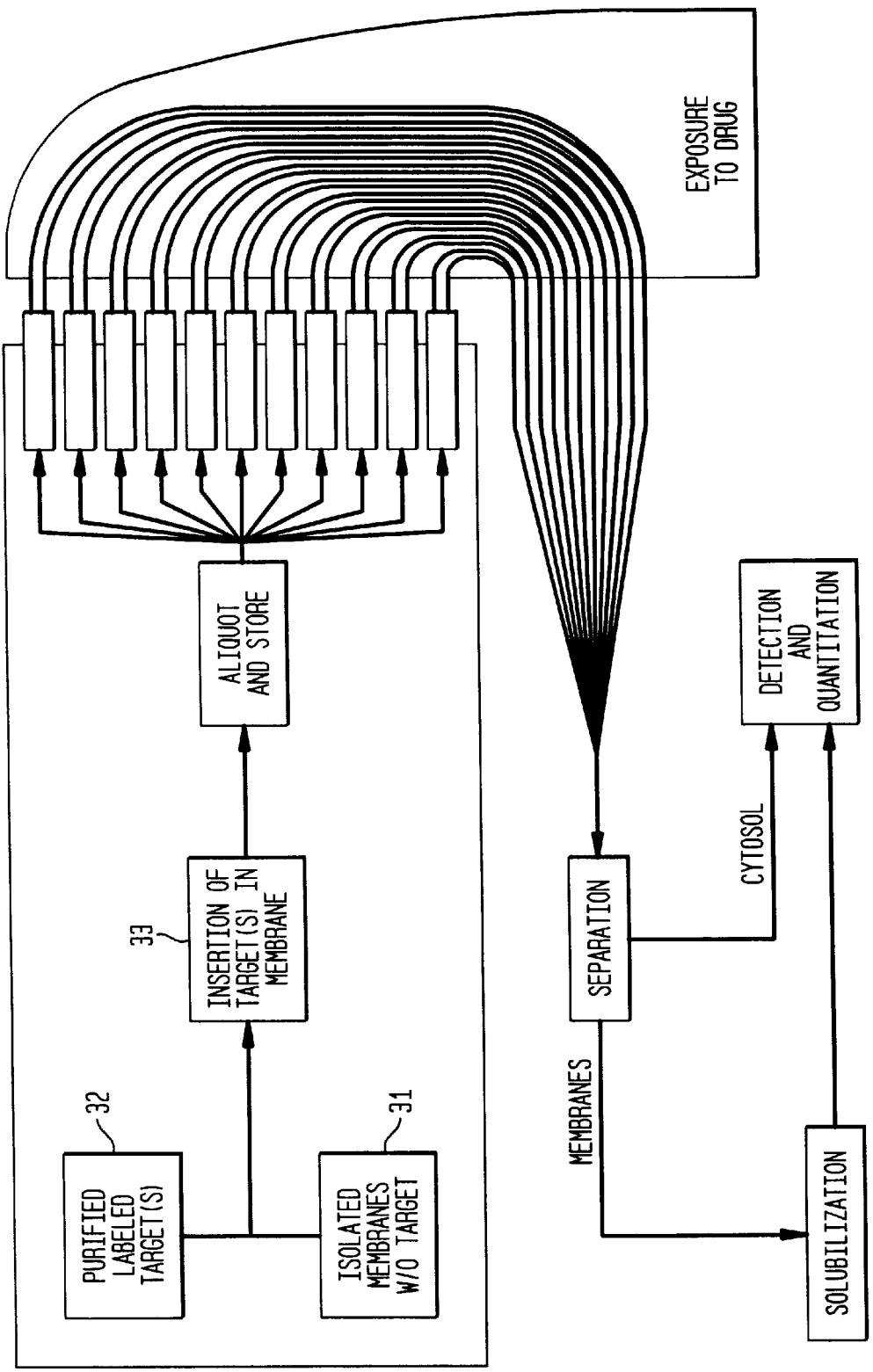
FIG. 15 is a flow chart diagraming the cell free assay for effect of drug on chemically labeled purified target anchored to purified membrane ex vitro of embodiment VII.

Embodiment VII
Cell Free Assay for Effect of Drug on Chemically Labeled Purified Target Anchored to Purified Membrane Ex Vitro As the final example presented herein, embodiment VII capitalizes on the inherent versatility of the cell free assay of embodiment I, supra. Here, referring to FIG. 15 the starting material is an isolated membranes 31 that lacks target and at least one purified target 32. Each purified target 32 is chemically labeled with a unique tag, for example Ras is labeled with FITC and oncogenic Ras is labeled with PE. The starting materials are simply combined and incubated at a target insertion step 33 to allow the target(s) to insert into the membrane. The drug screen then proceeds as in embodiment I, FIG. 9, supra.

One potential advantage for using this embodiment is that two forms of the same target, or two very closely related targets can be screened simultaneously and the difference in how drug effects their anchorage can be directly determined.

Having described preferred embodiments of the invention with reference to the accompanying drawings, it is to be understood that the invention is not limited to those precise embodiments, and that various changes and modifications may be effected thereinby one skilled in the art without departing from the scope or spirit of the invention as defined in the appended claims.

TABLE 1

References and Patents on the Significance of Myristoylation

Adams S P, Towler D A, and Gordon J I, Novel Inhibitor Peptides I, U.S. Pat. No. 4,778,878, Oct. 18, 1988.
Adams S P, Towler D A, and Gordon J I, Novel Inhibitor Peptides II, U.S. Pat. No. 4,778,877, Oct. 18, 1988.
Heuckeroth R O, Adams S P, and Gordon J I, Method of Inhibiting Virus, U.S. Pat. No. 5,073,571, Dec. 16, 1991.
Heuckeroth R O, Adams S P, Gordon J I, and Gokel G W, Novel Fatty Acid Analog Substrates, U.S. Pat. No. 5,082,967, Jan. 21, 1992.
Welply J K, Adams S P, and Gordon J I, Method of Inhibiting Parasitic Activity, U.S. Pat. No. 5,151,445, Sept. 29, 1992.
Gordon, J I, Anti-fungal Agent, U.S. Pat. No. 5,236,955, Aug. 17, 1993.
Devadas B, Gordon J I, and Adams S P, Azido-substituted Fatty Acid Analog Enzyme Substrates, U.S. Pat. No. 5,397,701, Mar. 14, 1995.
Duronio R J, Olins P O, and Gordon J I, Method of Protein N-myristoylation, U.S. Pat. No. 5,436,138, Jul. 25, 1995.
Duronio R J, Olins P O, and Gordon J I, Method of Protein N-myristoylation, U.S. Pat. No. 5,504,008, Apr. 2, 1996.
Devadas B, Gordon J I, and Adams S P, Triazolyl, Tetrazolyl, and Azido-substituted Fatty Acid Analog Enzyme Substrates, U.S. Pat. No. 5,338,858, Aug. 16, 1994.
Duronio R J, Jackson-Machelski E, Heuckeroth R O, Olins P O, Devine C S, Yonemoto W, Slice L W, Taylor S S, and Gordon J I, Protein N-myristoylation in *E. coli*: Reconstitution of a Eukaryotic Protein modification in Bacteria, Proc Natl Acad Sci USA Feb. 1990, 87: 1506–10.
Doering T L, Lu T, Werbovetz K A, Gokel G W, Hart G W, Gordon J I, and Englund P T, Toxicity of Myristic acid Toward African Trypanosomes, Proc Natl Acad Sci USA Oct. 1994, 91: 9735–9.
Doering T L, Raper J, Buxbaum L U, Adams S P, Gordon J I, Hart G W,

TABLE 1-continued

References and Patents on the Significance of Myristoylation and Englund PT, An Analog of Myristic Acid with Selective Toxicity for African Trypanosomes, Science June 1994, 252: 1851–4.
Duronio R J, Towler D A, Heuckeroth R O, and Gordon J I, Disruption of the Yeast N-Myristoyl Transferase Gene Causes Recessive Lethality, Science Feb. 1989, 243: 796–800.
Lodge J K, Jackson-Machelski E, Toffaletti D L, Perfect J R, and Gordon J I, Targeted Gene Replacement Demonstrates that Myristoyl-CoA:protein N-Myristoyl Transferase is essential for Viability of *Cryptococcus neoformans*, Proc Natl Acad Sci USA Dec. 1994, 91: 12008–12.
Weinberg R A, McWherter C A, Freeman S K, Wood D C, Gordon J I, and Lee S C, Genetic Studies Reveal that Myristoyl-CoA:protein N-Myristoyl Transferase is an essential enzyme in *Candida albicans*, Molecular Microbiology 1995, 16: 241–50.
Lagner C A, Lodge J K, Travis S J, Caldwell J E, Lu T, Li Q, Bryant M L, Devadas B, Gokel G W, Kobayashi G S and Gordon J I, 4-Oxatetradecanoic Acid is a Fungicidal for *Cryptococcus neoformans* and Inhibits Replication of Human Immunodefeciency Virus I, J Biol Chem 1992, 267: 17159–69.
Devadas B, Zupec M E, Freeman S K, Brown D L, Nagarajan S, Sikoriski J A, McWherter C A, Getman D P, and Gordon J I, Design and Synthesis of Potent and Selective Inhibitors of *Candida albicans* Myristoyl-CoA:protein N-Myristoyl Transferase, J Medicinal Chem 1995, 38: 1837–40.
Heukeroth R O, Glaser L, and Gordon J I, Heteroatom-substituted fatty acid analogs as substrates for N-Myristoyl Transferase: An approach for Studying both the Enzymology and Function of Protein Acylation, Proc Natl Acad Sci USA, Dec. 1988, 85: 8795–99.
Rudnick D A, McWherter C A, Rocque W J, Lennon P J, Getman D P, and Gordon J I, Kinetic and Structural Evidence for a Sequence Ordered Bi Bi Mechanism of Catalysis by *Saccharomyces cerevisiae* Myristoyl-CoA:protein N-Myristoyl Transferase, J Biol Chem, May 1991, 266: 9732–39.
Johnson D R, Cox A D, Solski P A, Devadas B, Adams S P, Leimgruber R M, Heuckeroth R O, Buss J E, and Gordon J I, Functional Analysis of Protein N-Myristoylation: Metabolic Labeling Studies using Three Oxygen Substituted Analogs of Myristic Acid and Cultured Mamalian Cells Provide Evidence for Protein-sequence-specific Incorporation and Analog-specific Redistribution, Proc Natl Acad Sci USA, Nov. 1990, 87: 8511–15.
Bryant M L, Heuckeroth R O, Kimata J T, Ratner L, and Gordon J I, Replication of Human Immunodeficiency Virus I and Moloney Murine Leukemia Virus is Inhibited by Different Heteroatom-containing Analogs of Myristic Acid, Proc Natl Acad Sci USA, Nov. 1989, 86: 8655–59.
Bryant M L, Ratner L, Duronio R J, Kishore N S, Devadas B, Adams S P, and Gordon J I, Incorporation of 12-methoxydodecanoate into the Human Immunodefeciency Virus I gag Polyprotein precursor inhibits its Proteolytic Processing and Virus Production in a Cronically Infected Human Lymphoid Cell Line, Proc Natl Acad Sci USA, Mar. 1991, 88: 2055–59.
Kishore N S, Lu T, Knoll L J, Katoh A, Rudnick D A, Mehta P P, Devadas B, Huhn M, Atwood J L, Adams S P, Gokel G W, and Gordon J I, The Substrate Specoificity of *Saccharomyces cerevisiae* Myristoyl-CoA:protein N-Myristoyltransferase, J Biol Chem, May 1991, 266: 8835–55.
Devadas B, Lu T, Katoh A, Kishore N S, Wade A C, Mehta P P, Rudnick D A, Bryant M L, Adams S P, Li Q, Gokel G W, and Gordon J I, Substrate Specoificity of *Saccharomyces cerevisiae* Myristoyl-CoA: protein N-Myristoyltransferase, J Biol Chem, April 1992, 267: 7724–39.
Rocque W J, McWherter C A, Wood D C, and Gordon J I, A comparative analysis of the Kenetic Mechanism and Peptide Substrate Specificity of Human and *Saccharomyces cerevisiae* Myristoyl-CoA:protein N-Myristoyltransferase, J Biol Chem, May 1993, 268: 9964–71.

TABLE 2

Patents issued to Farnesyl Protein Transferase (FPT) and FPT Inhibitors

| | U.S. Pat. No. | Title |
|---|---|---|
| 1 | 5,585,359 | Inhibitors of farnesyl-protein transferase |
| 2 | 5,578,629 | Benzamide-containing inhibitors of farnesyl-protein transferase |
| 3 | 5,576,313 | Inhibitors of farnesyl-protein transferase |
| 4 | 5,576,293 | Inhibitors of farnesyl-protein transferase |
| 5 | 5,571,835 | Inhibitors of farnesyl-protein transferase |
| 6 | 5,567,729 | Farnesyl compounds as farnesyl protein transferase inhibitors to treat ras induced tumor growth |
| 7 | 5,536,750 | Inhibitors of farnesyl-protein transferase |
| 8 | 5,534,537 | Prodrugs of inhibitors of farnesyl-protein transferase |
| 9 | 5,532,359 | Ras farnesyl transferase inhibitors |
| 10 | 5,525,479 | Fluorescence assay of Ras farnesyl protein transferase |
| 11 | 5,523,456 | Inhibitors of farnesyl-protein transferase |
| 12 | 5,523,430 | Protein farnesyl transferase inhibitors |
| 13 | 5,510,510 | Inhibitors of farnesyl protein transferase |
| 14 | 5,510,371 | Inhibitors of farnesyl-protein transferase |
| 15 | 5,506,262 | Cholesterol lowering compounds |
| 16 | 5,504,212 | Inhibitors of farnesyl-protein transferase |
| 17 | 5,504,115 | Inhibitors of farnesyl protein transferase |
| 18 | 5,498,627 | Octahydro-2-naphthalenecarboxylic acid derivative, its production and use |
| 19 | 5,491,164 | Inhibitors of farnesyl-protein transferase |
| 20 | 5,480,893 | Inhibitors of farnesyl protein transferase |
| 21 | 5,470,832 | Inhibitors of geranylgeranyl-protein transferase |
| 22 | 5,468,733 | Inhibitors of farnesyl-protein transferase |
| 23 | 5,447,717 | Cholesterol-lowering agents |
| 24 | 5,439,918 | Inhibitors of farnesyl-protein transferase |
| 25 | 5,436,263 | Inhibitors of farnesyl-protein transferase |
| 26 | 5,420,334 | Inhibitors of farnesyl-protein transferase |
| 27 | 5,420,245 | Tetrapeptide-based inhibitors of farnesyl transferase |
| 28 | 5,420,157 | Inhibitors of farnesyl protein transferase or prodrugs thereof |
| 29 | 5,369,125 | Cholesterol-lowering agents |
| 30 | 5,366,871 | Ubiquitin-peptide extensions as enzyme substrates |
| 31 | 5,364,948 | Biologically active compounds isolated from aerobic fermentation of *Trichoderma viride* |
| 32 | 5,362,906 | Farnesyl pyrophosphate analogs |
| 33 | 5,352,705 | Inhibitors of farnesyl protein transferase |
| 34 | 5,350,867 | Inhibitors of farnesyl protein transferase |
| 35 | 5,340,828 | Inhibitors of farnesyl protein transferase |
| 36 | 5,326,773 | Inhibitors of farnesyl-protein transferase |
| 37 | 5,298,655 | Farnesyl pyrophosphate analogs |
| 38 | 5,294,627 | Directed biosynthesis of biologically active compounds |
| 39 | 5,283,256 | Cholesterol-lowering agents |
| 40 | 5,260,479 | Inhibitors of farnesyl protein transferase |
| 41 | 5,260,465 | Inhibitors of farnesyl protein transferase |
| 42 | 5,258,401 | Cholesterol lowering compounds |
| 43 | 5,245,061 | Inhibitors of farnesyl protein transferase |
| 44 | 5,238,922 | Inhibitors of farnesyl protein transferase |
| 45 | 5,185,248 | Farnesyl-protein transferase assay for identifying compounds that block neoplastic transformation |
| 46 | 5,141,851 | Isolated farnesyl protein transferase enzyme |

TABLE 3

References to the Significance of Palmitoylation

Biewenga J E, Schrama L H, and Gispen W H, Presynaptic phosphoprotein B-50/GAP-43 in neuronal and synaptic plasticity, Acta Biochim Pol 1996, 43(2): 327–38;
De Vries L, Elenko E, Hubler L, Jones T L, and Farquhar MG, GAIP is membrane-anchored by palmitoylation and interacts with the activated (GTP-bound) form of G alpha i subunits, Proc Natl Acad Sci USA Dec. 24, 1996, 93(26): 15203–8;
Westrop G D, Hormozi E K, Da Costa N A, Parton R, and Coote J G, *Bordetella pertussis* adenylate cyclase toxin: proCyaA and CyaC proteins synthesised separately in *Escherichia coli* produce active toxin in vitro, Gene Nov. 21, 1996, 180(1–2): 91–9;
Iiri T, Backlund P S Jr, Jones T L, Wedegaertner P B, and Bourne H R, Reciprocal regulation of Gs alpha by palmitate and the beta gamma subunit, Proc Natl Acad Sci USA Dec. 10, 1996, 93(25): 14592–7;
Schroth B, Philipp H C, Veit M, Schmidt M F, and Herrmann A, Deacylation of influenza virus hemagglutinin does not affect the kinetics of low pH induced membrane fusion, Pflugers Arch 1996, 431(6 Suppl 2):

TABLE 3-continued

References to the Significance of Palmitoylation

R257–8;
Loisel T P, Adam L, Hebert T E, and Bouvier M, Agonist stimulation increases the turnover rate of beta 2AR-bound palmitate and promotes receptor depalmitoylation, Biochemistry Dec. 10, 1996, 35(49): 15923–32;
Willumsen B M, Cox A D, Solski P A, Der C J, and Buss J E, Novel determinants of H-Ras plasma membrane localization and transformation, Oncogene Nov. 7, 1996, 13(9): 1901–9;
Grunewald S, Haase W, Reilander H, and Michel H, Glycosylation, palmitoylation, and localization of the human D2S receptor in baculovirus-infected insected cells, Biochemistry Dec. 3, 1996, 35(48): 15149–61;
Fukushima Y, and Sugano K, Structural analysis of the histamine H2 receptor, Nippon Rinsho Apr. 1996, 54(4): 1144–8;
Laakkonen P, Ahola T, and Kaariainen L, The effects of palmitoylation on membrane association of Semliki forest virus RNA capping enzyme, J Biol Chem Nov. 8, 1996, 271(45): 28567–71;
Shum L, Turck C W, and Derynck R, Cysteines 153 and 154 of transmembrane transforming growth factor-alpha are palmitoylated and mediate cytoplasmic protein association, J Biol Chem Nov. 8, 1996, 271(45): 28502–8;
Song J, and Dohlman H G, Partial constitutive activation of pheromone responses by a palmitoylation-site mutant of a G protein alpha subunit in yeast, Biochemistry Nov. 26, 1996, 35(47): 14806–17;
Qanbar R, Cheng S, Possmayer F, and Schurch S, Role of the palmitoylation of surfactant-associated protein C in surfactant film formation and stability, Am J Physiol Oct 1996, 271(4 Pt 1): L572–80;
Baillie A G S, Coburn C T, and Abumrad N A, Reversible binding of long-chain fatty acids to purified FAT, the adipose CD36 homolog, J Membr Biol Sep 1996, 153(1): 75–81;
Doerrler W T, Ye J, Falck J R, and Lehrman M A, Acylation of glucosaminyl phosphatidylinositol revisited, Palmitoyl-CoA dependent palmitoylation of the inositol residue of a synthetic dioctanoyl glucosaminyl phosphatidylinositol by hamster membranes permits efficient mannosylation of the glucosamine residue, J Biol Chem Oct. 25, 1996, 271(43): 27031–8;
Chien A J, Carr K M, Shirokov R E, Rios E, and Hosey M M, Identification of palmitoylation sites within the L-type calcium channel beta2a subunit and effects on channel function, J Biol Chem Oct. 25, 1996, 271(43): 26465–8;
Duncan J A, and Gilman A G. Autoacylation of G protein alpha subunits, J Biol Chem Sep. 20, 1996, 271(38): 23594–600;
Liu L, Dudler T, and Gelb M H, Purification of a protein palmitoyl-transferase that acts on H-Ras protein and on a C-terminal N-Ras peptide, J Biol Chem Sep. 20, 1996, 271(38): 23269–76;
Tao N, Wagner S J, and Lublin D M, CD36 is palmitoylated on both N- and C-terminal cytoplasmic tails, J Biol Chem Sep. 13, 1996, 271(37): 22315–20;
Liu J, Garcia-Cardena G, and Sessa W C, Palmitoylation of endothelial nitric oxide synthase is necessary for optimal stimulated release of nitric oxide: implications for caveolae localization, Biochemistry Oct. 15, 1996, 35(41): 13277–81;
Moffett S, Adam L, Bonin H, Loisel T P, Bouvier M, and Mouillac B, Palmitoylated cysteine 341 modulates phosphorylation of the beta2-adrenergic receptor by the cAMP-dependent protein kinase, J Biol Chem Aug. 30, 1996, 271(35): 21490–7;
Horstmeyer A, Cramer H, Sauer T, Muller-Esterl W, and Schroeder C, Palmitoylation of endothelin receptor A. Differential modulation of signal transduction activity by post-translational modification, J Biol Chem Aug. 23, 1996, 271(34): 20811–9;
Chapman E R, Blasi J, An S, Brose N, Johnston P A, Sudhof T C, and Jahn R, Fatty acylation of synaptotagmin in PC12 cells and synaptosomes, Biochem Biophys Res Commun Aug. 5, 1996, 225(1): 326–32;
Palmer T M, Benovic J L, and Stiles G L, Molecular basis for subtype-specific desensitization of inhibitory adenosine receptors. Analysis of a chimeric A1–A3 adenosine receptor, J Biol Chem Jun. 21, 1996, 271(25): 15272–8;
Monier S, Dietzen D J, Hastings W R, Lublin D M, and Kurzchalia T V, Oligomerization of VIP21-caveolin in vitro is stabilized by long chain fatty acylation or cholesterol, FEBS Lett Jun. 17, 1996, 388(2–3): 143–9;
Garcia-Cardena G, Oh P, Liu J, Schnitzer J E, and Sessa W C, Targeting of nitric oxide synthase to endothelial cell caveolae via palmitoylation: implications for nitric oxide signaling, Proc Natl Acad Sci USA Jun. 25, 1996, 93(13): 6448–53;
Yang C, and Compans R W, Palmitoylation of the murine leukemia virus envelope glycoprotein transmembrane subunits, Virology Jul. 1, 1996, 221(1): 87–97;

TABLE 3-continued

References to the Significance of Palmitoylation

Rokaw M D, Benos D J, Palevsky P M, Cunningham S A, West M E, and Johnson J P, Regulation of a sodium channel-associated G-protein by aldosterone, J Biol Chem Feb. 23, 1996, 271(8): 4491–6;
Foissac X, Saillard C, Gandar J, Zreik L, and Bove J M, Spiralin polymorphism in strains of *Spiroplasma citri* is not due to differences in posttranslational palmitoylation, J Bacteriol May 1996, 178(10): 2934–40;
Dudler T, and Gelb M H, Palmitoylation of Ha-Ras facilitates membrane binding, activation of downstream effectors, and meiotic maturation in *Xenopus oocytes*, J Biol Chem May 10, 1996, 271(19): 11541–7;
Kosugi S, and Mori T, Cysteine-699, a possible palmitoylation site of the thyrotropin receptor, is not crucial for cAMP or phosphoinositide signaling but is necessary for full surface expression, Biochem Biophys Res Commun Apr. 25, 1996, 221(3): 636–40; and
Veit M, Sollner T H, and Rothman J E, Multiple palmitoylation of synaptotagmin and the t-SNARE SNAP-25, FEBS Lett Apr. 29, 1996, 385(1–2): 119–23;

TABLE 4

Specificity of Ras dislodging from membranes in the cell-free assay

| Compound | Dislodging of Ras (% of control) in a cell free system (10 $\mu$M drug) | Inhibition of EJ cells Growth $EC_{50}$ ($\mu$M) |
|---|---|---|
| | Inhibition of EJ cells Growth $EC_{50}$ ($\mu$M) | |
| FTS | 56 | 7.5 ± 3.7 |
| 5-Cl-FTS (RT-2) | 87 | 8.5 ± 2.4 |
| 4-Cl-FTS (RT-3) | 85 | 28.0 ± 3.0 |
| 3-Cl-FTS (RT-4) | 109 | >50 $\mu$M |
| FMTS (RT-5) | 110 | Not active at 50 $\mu$M |
| GTS | 100 | Not active at 50 $\mu$M |
| AFC | 100 | Not active at 50 $\mu$M |

What is claimed is:

1. A method of identifying compounds that disrupt binding of a membrane to a prenylated protein whose biological activity is dependent upon localization to the membrane, said method comprising:

a) providing an assay material comprising a specific membrane and a specific membrane anchored target prenylated protein, wherein biological activity of the prenylated protein is dependent upon localization to the membrane;

b) exposing the assay material to a compound; and c) determining fraction of the prenylated protein released from the specific membrane.

2. A method of identifying compounds that disrupt binding of a membrane to a ras protein whose biological activity is dependent upon localization to the membrane, said method comprising:

a) providing an assay material comprising a specific membrane and a specific membrane anchored ras protein, wherein biological activity of the ras protein is dependent upon localization to the membrane;

b) exposing the assay material to a compound; and c) determining fraction of the ras protein released from the specific membrane.

3. The method of claim 1 or claim 2 further comprising separating said assay material into a membrane fraction of said specific membrane and a non-membrane fraction of said assay material remaining after said specific membrane is removed.

4. The method of claim 3 wherein said determining the fraction of protein released from the specific membrane comprises measuring a fraction of protein in the non-membrane fraction.

5. The method of claim 3 wherein said determining fraction of protein released from the specific membrane comprises measuring a fraction of protein in the membrane fraction.

6. The method of claim 1 or claim 2 wherein the protein carries a tag that allows the protein to be detected.

7. The method of claim 6 wherein the tag comprises a green fluorescent protein, Alkaline Phosphatase, Horseradish Peroxidase, Urease, f3-galactosidase, CAT, Luciferase, an immunogenic tag peptide sequence, an extrinsically activatable enzyme, an extrinsically activatable toxin, an extrinsically activatable fluor, an extrinsically activatable quenching agent, a radioactive element or an antibody.

8. The method of claim 1 or claim 2 wherein said specific membrane is selected from the group consisting of a plasma membrane, a nuclear membrane, endoplasmic reticulum, a golgi and a vesicle.

9. The method of claim 1 wherein the prenylated protein carries a farnesyl group, a geranyl group or a geranylgeranyl group.

10. The method of claim 1 wherein the prenylated protein is selected from the group consisting of Rap proteins, Ral proteins, Rho proteins, Ran proteins and Rab/Ypt proteins.

11. The method of claim 2 wherein the ras protein is an H-ras, N-ras, Ka-ras or Kb-ras protein.

12. The method of claim 2 wherein the ras protein carries a prenyl group.

13. The method of claim 2 wherein the ras protein carries a palmitoyl group.

14. The method of claim 1 or claim 2 wherein the compound is being tested for anti-cancer activity.

15. The method of claim 1 or claim 2 wherein said assay material is cell-free.

16. The method of claim 1 or claim 2 wherein said assay material comprises a cell culture.

17. The method of claim 1 or claim 2 which is conducted in vivo.

18. The method of claim 17 wherein said assay material comprises a transgenic animal.

19. A method of testing a compound for effect on specific prenylated protein or ras protein membrane anchorage, comprising:

labeling said protein with a tag;
exposing said membrane anchorage to said compound; and
at least one of detecting a membrane-dissociated tag concentration and detecting a membrane associated tag concentration.

20. The method of claim 19 wherein the tag comprises a green fluorescent protein, Alkaline Phosphatase, Horseradish Peroxidase, Urease, f3-galactosidase, CAT, Luciferase, an immunogenic tag peptide sequence, an extrinsically activatable enzyme, an extrinsically activatable toxin, an extrinsically activatable fluor, an extrinsically activatable quenching agent, a radioactive element or an antibody.

21. The method of claim 19 wherein said specific membrane is selected from the group consisting of a plasma membrane, a nuclear membrane, endoplasmic reticulum, a golgi and a vesicle.

22. The method of claim 19 wherein the prenylated protein carries a farnesyl group, a geranyl group or a geranylgeranyl group.

23. The method of claim 22 wherein the prenylated protein is selected from the group consisting of Rap proteins, Ral proteins, Rho proteins, Ran proteins and Rab/Ypt proteins.

24. The method of claim 19 wherein the ras protein is an H-ras, N-ras, Ka-ras or Kb-ras protein.

25. The method of claim 19 wherein the ras protein carries a prenyl group.

26. The method of claim 19 wherein the ras protein carries a palmitoyl group.

27. The method of claim 19 wherein the compound is being tested for anti-cancer activity.

28. The method of claim 19 which is conducted in a cell-free environment.

29. The method of claim 19 wherein said assay material comprises a cell culture.

30. The method of claim 19 which is conducted in vivo.

31. The method of claim 30 wherein said assay material comprises a transgenic animal.

32. The method of claim 19 wherein the effect comprises extent of dislodgment of the protein from the membrane.

33. The method of claim 19 wherein the effect comprises extent of degradation of protein dislodged from the membrane.

* * * * *

UNITED STATES PATENT AND TRADEMARK OFFICE
CERTIFICATE OF CORRECTION

PATENT NO. : 6,492,128 B1
DATED : December 10, 2002
INVENTOR(S) : Roni Haklai, Ariella Paz and Yoel Kloog It is certified that error appears in the above-identified patent and that said Letters Patent is hereby corrected as shown below:

Title page,
Item [57], ABSTRACT,
Line 2, "dependant" should read -- dependent --.
Line 7, "are" should read -- is --.

Column 1,
Line 63, "are" should read -- is --.

Column 2,
Line 23, "activating" should read -- activated --.
Line 31, "define" should read -- defines --.

Column 3,
Line 7, "are" should read -- is --.
Line 7, "have" should read -- has --.
Line 17, "are" should read -- is --.

Column 5,
Line 44, "are" should read -- is --.

Column 6,
Line 1, "examples" should read -- demonstrate --.

Column 8,
Line 53, "are" should read -- is --.

Column 16,
Line 32, delete "," after "A".

Column 19,
Line 21, "are" should read -- is --.

Column 21,
Line 57, "combine" should read -- combined --.

Column 23,
Line 15, insert "." after "motif".

UNITED STATES PATENT AND TRADEMARK OFFICE
CERTIFICATE OF CORRECTION

PATENT NO.    : 6,492,128 B1
DATED         : December 10, 2002
INVENTOR(S)   : Roni Haklai, Ariella Paz and Yoel Kloog It is certified that error appears in the above-identified patent and that said Letters Patent is hereby corrected as shown below:

<u>Column 24,</u>
Line 36, "thereinby" should read -- therein by --.

Signed and Sealed this

Eleventh Day of March, 2003

JAMES E. ROGAN
*Director of the United States Patent and Trademark Office*